(12) United States Patent
Croce

(10) Patent No.: US 7,667,090 B2
(45) Date of Patent: Feb. 23, 2010

(54) TRANSGENIC MOUSE MODEL OF B CELL MALIGNANCY

(75) Inventor: Carlo M. Croce, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 12/298,221

(22) PCT Filed: Apr. 24, 2007

(86) PCT No.: PCT/US2007/009910

§ 371 (c)(1),
(2), (4) Date: Nov. 10, 2008

(87) PCT Pub. No.: WO2007/127190

PCT Pub. Date: Nov. 8, 2007

(65) Prior Publication Data

US 2009/0222934 A1    Sep. 3, 2009

Related U.S. Application Data

(60) Provisional application No. 60/745,454, filed on Apr. 24, 2006.

(51) Int. Cl.
*A01K 67/027* (2006.01)
*G01N 33/00* (2006.01)
*C12N 15/00* (2006.01)

(52) U.S. Cl. ................................ 800/18; 800/3; 800/21
(58) Field of Classification Search ..................... 800/3, 800/18, 21
See application file for complete search history.

(56) References Cited

OTHER PUBLICATIONS

Bichi (PNAS, May 14, 2002, vol. 99, No. 10, p. 6955-6960).*
Eis (PNAS, Mar. 8, 2005, vol. 102, No. 10, p. 3627-3632).*
PCT/US2007/009910 International Preliminary Report on Patentability dated Nov. 6, 2008.
PCT/US2007/009910 Search Report and Written Opinion dated Feb. 13, 2008.
Bichi et al., Human chronic lymphocytic leukemia modeled in mouse by targeted TCL1 expression, PNAS, 2002, vol. 99, No. 10, pp. 6955-6960.

* cited by examiner

*Primary Examiner*—Michael C. Wilson
(74) *Attorney, Agent, or Firm*—MacMillan, Sobanski & Todd, LLC

(57) ABSTRACT

A transgenic non-human animal, such as a mouse, has a genome that include a nucleic acid construct having at least one transcriptional regulatory sequence capable of directing expression in B cells of the animal, wherein the transcriptional regulatory sequence is operably linked to a nucleic acid encoding a miR155 gene product. A method of testing the therapeutic efficacy of an agent in treating or preventing a lymphoproliferative condition includes assessing the effect(s) of the agent on a transgenic non-human animal.

22 Claims, 9 Drawing Sheets

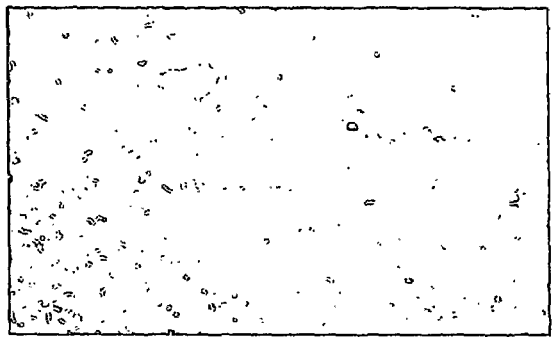
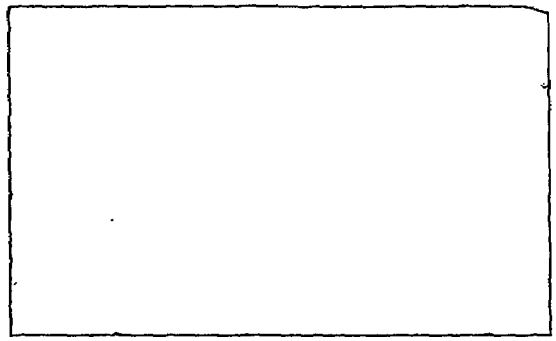
Figure 5A
Figure 5B
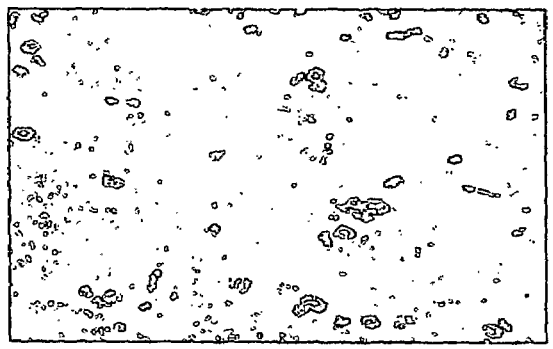
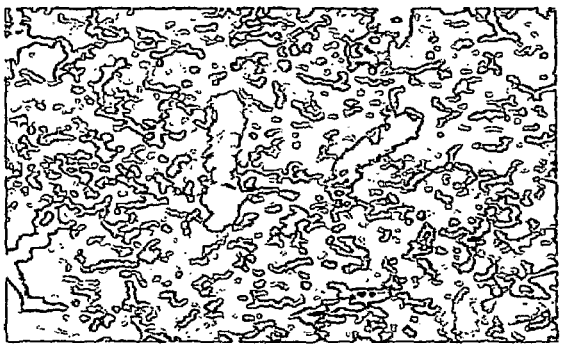
Figure 5C
Figure 5D
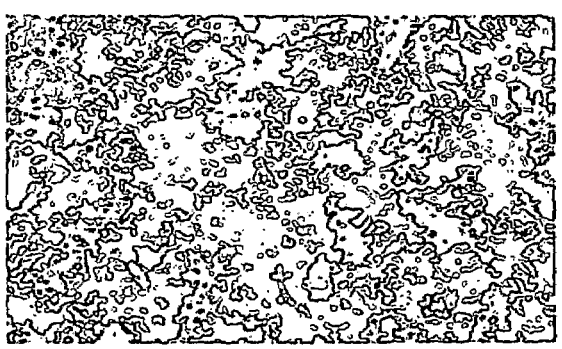
Figure 5E
Figure 5F

SEQUENCE LISTING

```
<160> NUMBER OF SEQ ID NOS: 7

<210> SEQ ID NO 1
<211> LENGTH: 65
<212> TYPE: RNA
<213> ORGANISM: Mus musculus

<400> SEQUENCE: 1
cuguuaaugc uaauugugau aggggguuuug gccucugacu gacuccuacc uguuagcauu     60
aacag                                                                  65

<210> SEQ ID NO 2
```

-continued

```
<211> LENGTH: 22
<212> TYPE: RNA
<213> ORGANISM: Mus musculus

<400> SEQUENCE: 2
uuaaugcuaa uugugauagg gg                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 3
tgaaggatct gccagaactg aa                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 4
tgcaatgctc agaaaactcc at                                              22

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:
      Synthetic primer

<400> SEQUENCE: 5

Lys Asp Glu Leu
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:
      Synthetic primer

<400> SEQUENCE: 6

Asp Glu Ala Asp
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:
      Synthetic primer

<400> SEQUENCE: 7

Asp Glu Ala His
1
```

TRANSGENIC MOUSE MODEL OF B CELL MALIGNANCY

The present invention claims the benefit of the PCT/US07/009,910 filed Apr. 24, 2007, which claims priority to the provisional patent application Ser. No. 60/745,454 filed Apr. 24, 2006. This application contains a Sequence Listing submitted as an electronic ASCII text file via EFS-Web named "604_28352_Seqlist_OSURF_06141.txt", having a size in bytes of 2 kb, and created on Feb. 4, 2009. This information is identical to the Sequence Listing filed in the above-identified PCT application. The information contained in this electronic file is hereby incorporated by reference in its entirety pursuant to 37 CFR §1.52(e)(5).

GOVERNMENT SUPPORT

The invention was supported, in whole or in part, by a grant from the U.S. Government under P01 CA076259, P01 CA081534, CA016058 and CA016672 awarded by the National Institutes of Health. The Government has certain rights in the invention.

BACKGROUND OF THE INVENTION

Acute leukemia is a rapidly progressive malignant disease of the bone marrow and blood that results in the accumulation of immature, functionless cells, called blast cells, in the marrow and blood. The accumulation of blast cells in the marrow blocks normal blood cell development. As a result, red cells, white cells and platelets are not produced in sufficient numbers. When the disease originates in a marrow lymphocyte progenitor cell, it results in acute lymphoblastic leukemia (ALL) and when the disease originates in a myeloid progenitor, it results in acute myelogenous leukemia (AML).

ALL is a rapidly progressive cancer that starts by the malignant transformation of a marrow lymphocyte. ALL is the most common type of childhood leukemia, with 3,000 new cases per year in all age groups. The transformed, now malignant, cell multiplies and accumulates in the marrow as leukemic lymphoblasts. The lymphoblasts block normal blood cell-formation in the marrow, resulting in insufficient production of red cells, white cells and platelets.

High-grade lymphomas, also known as aggressive lymphoma, include several subtypes of lymphoma that progress relatively rapidly if untreated. These subtypes include, e.g., AIDS-associated lymphoma, anaplastic large cell lymphoma, Burkitt's lymphoma, diffuse large cell lymphoma, immunoblastic lymphoma, lymphoblastic lymphoma and small non-cleaved cell lymphomas. Compared to diffuse large B-cell lymphomas, high-grade lymphomas behave more aggressively, require more intensive chemotherapy, and occur more often in children. Because rapidly dividing cells are more sensitive to anti-cancer agents and because the young patients usually lack other health problems, some of these lymphomas show a dramatic response to therapy. Acute lymphoblastic leukemia and high-grade lymphoma are the most common leukemias and lymphomas in children. These diseases are, for the most part, polyclonal, suggesting that only a few genetic changes are sufficient to induce malignancy.

MicroRNAs (miRNAs) represent a new class of abundant small RNAs that play important regulatory roles at the post-transcriptional level by binding to targeted mRNAs and either blocking their translation or initiating their degradation, according to the degree of complementarity with the target. Since their discovery in 1993 in *Caenorhabditis elegans* (Lee, R. et al., *Cell* 75:843-854 (1993)), there have been numerous reports that implicated these tiny molecules in the posttranscriptional regulation of a large array of proteins with very diverse roles, ranging from cell proliferation and differentiation to lipid metabolism (Nairz, K., et al., *Dev. Biol.* 291:314-324 (2006); Chen, J. F., et al., *Nat. Genet.* 38:228-233 (2006); Naguibneva, I., et al., *Nat. Cell Biol.* 8:278-284 (2006); Esau, C., et al., *Cell Metab.* 3:87-98 (2006); and Gauthier, B. R., et al., *Nat. Med.* 12:36-18 (2006)).

miRNA profiling of hematopoietic lineages in humans and mice showed that miRNAs are differentially expressed in the course of hematopoietic development, suggesting a potential role in hematopoietic differentiation (Chen, C. Z., et al., *Science* 303:83-86 (2004); Chen, C. Z., et al., *Semin. Immunol.* 17:155-165 (2005); and Ramkissoon, S. H., et al., *Leuk. Res.* 30:643-647 (2006)). We have shown that miR-15a and miR-16-1 are deleted or down-regulated in 68% of cases of chronic lymphocytic leukemia (CLL) (Calin, G. A., et al., *Proc. Natl. Acad. Sci. USA* 99:15524-15529 (2002); and Calin, G. A., et al., *Proc. Natl. Acad. Sci. USA* 101:11755-11760 (2004)), and that miRNAs genes are frequently located at fragile sites and genomic regions involved in cancers (Calin, G. A., et al, *Proc. Natl. Acad. Sci. USA* 101:2999-3004 (2004)). miR155 and BIC (its host gene) transcripts have been shown to accumulate in human B cell lymphomas, especially diffuse large B cell lymphomas (Eis, P. S., et al, *Proc. Natl. Acad. Sci. USA* 102:3627-3632 (2005)), Hodgkin lymphomas (Kluvier, J., et al., *J. Pathol* 207:243-249 (2006)), and certain types of Burkitt lymphomas (latency type III Epstein-Barr virus-positive Burkitt lymphoma) (Kluvier, J., et al, *Genes Chromosomes Cancer* 45: 147-153 (2006)).

Currently, there is an urgent need to produce animal models that can be used to screen for, and identify, candidate agents that have therapeutic potential for the treatment of lymphoproliferative disorders, such as B cell malignancies (e.g., B cell leukemias, B cell lymphomas).

SUMMARY OF THE INVENTION

The present invention is based on the discovery that transgenic mice carrying a miR155 transgene, whose expression is targeted to B cells (e.g., using an Ig heavy chain-Eμ enhancer), initially exhibit a preleukemic pre-B cell proliferation, evident in spleen and bone marrow, and later develop B cell malignancies. Transgenic mice that overexpress miR155 develop a lymphoproliferative disease resembling human lymphoproliferative diseases, thus strongly implicating miR155 in the initiation and/or progression of these diseases. The Eμ-mmu-miR155 transgenic mice are useful for devising new therapeutic approaches to treat different forms of lymphoproliferative disorders, such as B cell malignancies (e.g., acute lymphoblastic leukemia, high-grade lymphomas) in humans.

Accordingly, in one aspect, there is provided herein, novel animal models for lymphoproliferative disorders. Specifically, according to one aspect, animal models for B cell malignancies (e.g., leukemias (e.g., acute lymphoblastic leukemia), lymphomas (e.g., high-grade lymphoma), and neoplasms) are provided.

In one embodiment, there is provided herein a transgenic non-human animal (e.g., a mouse) whose genome comprises a nucleic acid construct comprising at least one transcriptional regulatory sequence capable of directing expression in B cells of the animal, operably linked to a nucleic acid encoding a miR155 gene product. In a particular embodiment, the miR155 gene product comprises a nucleotide sequence having at least 90% sequence identity to SEQ ID NO:1 and/or SEQ ID NO:2. In another embodiment, the miR155 gene product comprises the nucleotide sequence of SEQ ID NO:1.

In still another embodiment, the miR155 gene product comprises the nucleotide sequence of SEQ ID NO:2.

According to one embodiment, the at least one transcriptional regulatory sequence can be any sequence capable of directing expression in B cells of the animal. In one embodiment, the transcriptional regulatory sequence comprises a $V_H$ promoter (e.g., a $V_H$ promoter derived from mouse). In another embodiment the transcriptional regulatory sequence comprises an Ig heavy chain-Eµ enhancer (e.g., an Ig heavy chain-Eµ enhancer derived from mouse). In a related embodiment, the nucleic acid construct comprises the 3' UTR and poly(A) sequence of a β-globin gene (e.g., a β-globin gene derived from human or other mammalian species).

There is also provided herein a transgenic non-human animal whose genome comprises a nucleic acid construct comprising a $V_H$ promoter and an Ig heavy chain-Eµ enhancer, operably linked to a nucleic acid encoding a miR155 gene product comprising SEQ ID NO:1 and/or SEQ ID NO:2. In a particular embodiment, the transgenic non-human animal's genome comprises a nucleic acid construct comprising a $V_H$ promoter and an Ig heavy chain-Eµ enhancer, operably linked to a nucleic acid encoding a miR155 gene product comprising a nucleotide sequence having at least 90% sequence identity to SEQ ID NO:1 and/or SEQ ID NO:2.

In a particular embodiment, the transgenic non-human animal has an expanded population of B220low/CD19$^{low}$/CD10$^{low}$/IgM$^-$/TCR$^-$/CD43$^-$ lymphoid cells in the spleen, the bone marrow or both the spleen and bone marrow, relative to this population in a suitable control animal. In a related embodiment, the transgenic non-human animal exhibits a lymphoproliferative condition. In a certain embodiment, the lymphoproliferative condition is a B cell malignancy (e.g., a B cell leukemia, for example, acute lymphoblastic leukemia; a B cell lymphoma, a B cell neoplasm). In a further embodiment, the B cell malignancy exhibits characteristics of human acute lymphoblastic leukemia, human lymphoblastic lymphoma or a combination thereof. In yet another embodiment, the lymphoproliferative condition is a preleukemic state (e.g., pre-B cell proliferation). In additional embodiments, the transgenic non-human animal exhibits an enlarged abdomen, splenomegaly, bone marrow replacement, lymphopenia, or a combination thereof.

There is also provided herein a method of testing the therapeutic efficacy of an agent in treating or preventing a lymphoproliferative condition in a subject. According to one embodiment, the method comprises administering the agent to a transgenic non-human animal (e.g., a mouse) whose genome comprises a nucleic acid construct comprising at least one transcriptional regulatory sequence capable of directing expression in B cells of the animal (e.g., a $V_H$ promoter, an Ig heavy chain-Eµ enhancer, a combination thereof), wherein the transcriptional regulatory sequence is operably linked to a nucleic acid encoding a miR155 gene product comprising a nucleotide sequence having at least 90% sequence identity to SEQ ID NO:1 and/or SEQ ID NO:2. In a particular embodiment, the miR155 gene product comprises the nucleotide sequence of SEQ ID NO:1. In another embodiment, the miR155 gene product comprises the nucleotide sequence of SEQ ID NO:2.

After the agent has been administered to the transgenic animal, one or more symptoms and/or indications of the lymphoproliferative condition in the transgenic animal are compared with those of a control animal of the same genotype, which has not been administered the agent. If the agent inhibits, prevents and/or reduces one or more symptoms and/or indications of the lymphoproliferative condition in the transgenic animal to which it has been administered, relative to the control animal, then the agent is considered to have therapeutic efficacy in treating or preventing a lymphoproliferative condition. In a certain embodiment, the one or more symptoms and/or indications of the lymphoproliferative condition are selected from the group consisting of: an expanded population of B220$^{low}$/cD19$^{low}$/CD10$^{low}$/IgM$^-$/TCR$^-$/CD43$^-$ lymphoid cells, an enlarged abdomen, splenomegaly, bone marrow replacement, lymphopenia and a combination thereof.

In another embodiment, there is provided herein a method of determining whether an agent affects a lymphoproliferative condition in a subject (e.g., affecting a difference in the detectability and/or rate of appearance of one or more symptoms and/or indications of a lymphoproliferative condition). The method comprises administering an agent to a transgenic non-human animal described herein and comparing one or more symptoms and/or indications of the lymphoproliferative condition in the transgenic animal to those of a control animal of the same genotype, wherein the control animal has not been administered the agent. Detection of a difference in the detectability and/or rate of appearance of one or more symptoms and/or indications of the lymphoproliferative condition in the transgenic animal, relative to the control animal, is indicative of the agent affecting the lymphoproliferative condition.

In one embodiment, the lymphoproliferative condition is a B cell malignancy. In a particular embodiment, the B cell malignancy is selected from the group consisting of acute lymphoblastic leukemia, B cell lymphoma (e.g., high-grade lymphoma), B cell neoplasm and a combination thereof. The B cell malignancy may exhibit characteristics of human acute lymphoblastic leukemia, human lymphoblastic lymphoma or both. In another embodiment, the lymphoproliferative condition is a preleukemic state, such as a state characterized by pre-B cell proliferation.

These as well as other important aspects of the invention will become more apparent from the following detailed description.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5A is a micrograph depicting a hematoxylin/eosin (H&E)-stained section of spleen from a 3 week old transgenic mouse (mouse no. 50; founder no. 10) at 200× magnification. The section displays atypical lymphoid proliferation compressing the white pulp.

FIG. 5B is a micrograph depicting an H&E-stained section of spleen from a 6 month old transgenic mouse (founder no. 8) at 100× magnification. The overall architecture of the spleen is being replaced by atypical lymphoid proliferation. Only a few germinal lymphoid follicles remain, which are greatly decreased in size and compressed by the proliferation.

FIG. 5C is a micrograph depicting an H&E-stained section of spleen from a 6 month old transgenic mouse (founder no. 8) at 200× magnification. The spleen architecture has been almost completely effaced by the lymphoblastic proliferation. Remnants of 2 small compressed lymphoid follicles are visible.

FIG. 5D is a micrograph depicting an H&E-stained section of bone marrow from a 6 month old transgenic mouse (founder no. 8) at 400× magnification, showing the lymphoblastic proliferation in the bone marrow that leads to the replacement of the hemtopoietic foci.

FIG. 5E is a micrograph depicting an H&E-stained section of normal spleen at 200× magnification.

FIG. 5F is a micrograph depicting a section of spleen from a 3 week old transgenic mouse (mouse no. 72) at 200× magnification. The section has been stained for Ki67 and shows increased lymphoid proliferation in the spleen.

DETAILED DESCRIPTION OF THE INVENTION

Figure 1:
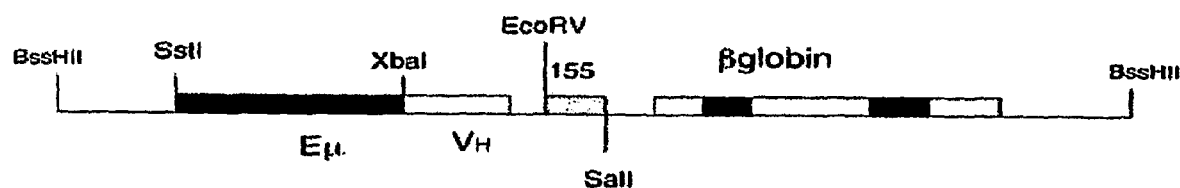
FIG. 1 is schematic diagram depicting the miR155 transgene construct that was injected in the male pronuclei of the oocytes of pregnant C57/B6 and FVB/N female mice. The miR155 transgene construct was made by inserting the mmu-miR155 gene between the EcoRV and SalI sites, downstream from the $V_H$ promoter Eµ enhancer.

A description of particular embodiments of the invention follows.

As exemplified and described herein, transgenic mice that overexpress the microRNA, miR155, develop a lymphoproliferative disease resembling acute lymphoblastic leukemia and high-grade lymphoma in humans. The results provided herein strongly indicate that oncogenic expression of miR155 and/or other gene(s) (e.g., genes that are activated in cancer (e.g., signal transduction genes)) are involved in the initiation and/or progression of B cell malignancies. Accordingly, there is provided herein an animal model that may be used to investigate the mechanisms underlying the initiation and progression of B cell malignancies and other lymphoproliferative conditions. This animal model may also be used in the identification, development and testing of novel therapeutic agents that are useful in treating or preventing lymphoproliferative disorders.

In one embodiment, there is provided herein a transgenic animal whose genome comprises a nucleic acid construct or transgene comprising at least one transcriptional regulatory sequence capable of directing expression to B cells, wherein the transcriptional regulatory sequence is operably linked to a nucleic acid sequence encoding a miR155 gene product. The term "transgene" refers to a nucleic acid sequence introduced into one or more cells of a non-human animal by way of human intervention, such as by way of the methods described herein. The introduced genetic information may be foreign to the species of animal to which the recipient belongs, foreign only to the particular individual recipient, or genetic information already possessed by the recipient. In the latter case, the introduced genetic information may be differentially-expressed, as compared to the native endogenous gene.

The transgenic non-human animals have a genome that comprises a nucleic acid construct/transgene, that is capable of expressing a miR155 gene product. As miR gene products, (also referred to herein as microRNAs, miRs and miRNAs) are not translated into protein, the term "miR gene product" does not include proteins. The unprocessed miR gene transcript is also called a "miR precursor," and typically comprises an RNA transcript of about 70-100 nucleotides in length. The miR precursor can be processed (e.g., through natural processing routes (e.g., using intact cells or cell lysates) or by synthetic processing routes (e.g., using isolated processing enzymes, such as isolated Dicer, Argonaut, or RNAse III (e.g., *E. coli* RNAse III)) into an active 19-25 nucleotide RNA molecule. This active 19-25 nucleotide RNA molecule is also called the "processed" miR gene transcript or "mature" miRNA. When a microRNA is referred to herein by name, the name corresponds to both the precursor and mature forms, unless otherwise indicated.

As used herein, "miR155 gene product" refers to the unprocessed (e.g., precursor) or processed (e.g., mature) RNA transcript from a miR155 gene, such as, but not limited to, a miR155 gene from mouse (*Mus musculus*). The precursor miR155 gene product from mouse is represented by the nucleotide sequence: 5'-CUGUUAAUGCUAAUU-GUGAUAGGGGUUUUGGCCU-CUGACUGACUCCUACCUGUUAGCAUUAACAG-3' (SEQ ID NO:1), while the processed, or mature, mouse miR155 gene product is represented by the nucleotide sequence: 5'-UUAAUGCUAAUUGUGAUAGGGG-3' (SEQ ID NO:2; GenBank Accession No. AJ459767).

In certain embodiments, the miR155 gene product comprises a nucleotide sequence having at least 70%, at least 75%, at least 80%, at least 85%, at least 90%, at least 95%, at least 99%, or 100%, sequence identity to the nucleotide sequences of SEQ ID NO:1 and/or SEQ ID NO:2. In a particular embodiment, the miR155 gene product comprises a nucleotide sequence having 100% identity to the nucleotide sequence of SEQ ID NO:1. In another embodiment, the miR155 gene product comprises a nucleotide sequence having 100% identity to the nucleotide sequence of SEQ ID NO:2.

The actual comparison of two sequences can be accomplished by well-known methods, for example, using a mathematical algorithm. A preferred, non-limiting example of such a mathematical algorithm is described in Karlin et al. (*Proc. Natl. Acad. Sci. USA,* 90:5873-5877 (1993)). Such an algorithm is incorporated into the BLASTN and BLASTX programs (version 2.2) as described in Schaffer et al. (*Nucleic Acids Res.,* 29:2994-3005 (2001)). When utilizing BLAST and Gapped BLAST programs, the default parameters of the respective programs (e.g., BLASTN; available at the Internet site for the National Center for Biotechnology Information) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys, San Diego, Calif.) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (Comput. Appl. Biosci., 10: 3-5, 1994); and FASTA described in Pearson and Lipman (Proc. Natl. Acad. Sci. USA, 85: 2444-2448, 1988).

In another embodiment, the percent identity between two amino acid sequences can be accomplished using the GAP program in the GCG software package (Accelrys, San Diego, Calif.) using either a Blossom 63 matrix or a PAM250 matrix, and a gap weight of 12, 10, 8, 6, or 4, and a length weight of 2, 3, or 4. In yet another embodiment, the percent identity between two nucleic acid sequences can be accomplished using the GAP program in the GCG software package (Accelrys, San Diego, Calif.), using a gap weight of 50 and a length weight of 3.

According to one aspect, the transgenic non-human animal possesses a genome that comprises a nucleic acid construct in which a nucleic acid sequence encoding a miR155 gene product is operably linked to at least one transcriptional regulatory sequence capable of directing expression in B cells of the animal. The term "transcriptional regulatory sequence" is used according to its art-recognized meaning. It is intended to mean any DNA sequence that can, by virtue of its sequence, cause the linked gene to be either up- or down-regulated in a particular cell. In the case of a promoter, the promoter will generally be adjacent to the coding region. In the case of an enhancer, however, the enhancer may function at some distance from the coding region, such that there is an intervening DNA sequence between the enhancer and the coding region. To direct expression of the genetic information, which may include a DNA sequence encoding a particular protein (or "coding region"), the coding region of interest may be coupled to at least one transcriptional regulatory sequence in a functional manner. Transcriptional regulatory sequences may be used to increase, decrease, regulate or designate to certain tissues or to certain stages of development, the expression of a gene. The transcriptional regulatory sequences need not be naturally occurring sequences.

Thus, in one embodiment described herein, a sequence encoding miR155 is operably linked to transcriptional regulatory sequence(s) directing expression to B cells, to generate a recombinant construct or transgene. The transcriptional regulatory sequence can be any sequence capable of directing expression in B cells. Examples of suitable transcriptional regulatory sequence include, but are not limited to, a $V_H$ promoter, an Ig heavy chain-Eµ enhancer and a combination thereof. In a particular embodiment, the transcriptional regulatory sequence is a mouse transcriptional regulatory sequence or a transcriptional regulatory sequence derived from mouse.

A nucleic acid molecule is said to be "capable of expressing" or "capable of directing expression of" a microRNA if it contains nucleotide sequence(s) that contain transcriptional regulatory information, and such sequencers) are "operably linked" to nucleotide sequence(s) that encode the microRNA. An operable linkage is a linkage in which regulatory nucleic acid sequence(s) and the nucleic acid sequence(s) sought to be expressed are connected in such a way as to permit gene expression.

In general, the regulatory regions needed for gene expression include, but are not limited to, transcriptional regulatory sequences (e.g., a promoter region, an enhancer region), as well as DNA sequence(s) that, when transcribed into RNA, contribute to the stability of the gene transcript.

The term "promoter" is used according to its art-recognized meaning. It is intended to mean the DNA region, usually upstream to the coding sequence of a gene or operon, which binds RNA polymerase and directs the enzyme to the correct transcriptional start site. A promoter region is operably linked to a DNA sequence if the promoter is capable of effecting transcription of that DNA sequence.

The term "enhancer" is used according to its art-recognized meaning. It is intended to mean a sequence found in eukaryotes and certain eukaryotic viruses, which can increase transcription from a gene when located (in either orientation) up to several kilobases from the gene being studied. These sequences usually act as enhancers when on the 5' side (upstream) of the gene in question. However, some enhancers are active when placed on the 3' side (downstream) of the gene. In some cases, enhancer elements can activate transcription from a gene with no (known) promoter.

The nucleic acid construct may also include sequences that promote expression and/or stability of the construct and/or a gene product expressed from the construct. In a particular embodiment, the nucleic acid construct comprises the 3' UTR and poly(A) sequence of a β-globin gene (e.g., a mouse β-globin gene). Other sequences that promote expression and/or stability of the construct and/or a gene product expressed from the construct are known in the art and are encompassed herein.

The term "transgenic non-human animal" is used herein to include all vertebrate animals, except humans. In one embodiment, the transgenic non-human animal is a mammal. Such transgenic non-human animals include, for example, transgenic pigs, transgenic rats, transgenic rabbits, transgenic cattle, transgenic goats, and other transgenic animal species, particularly mammalian species. Additionally, other members of the rodent family, e.g., rats, and guinea pigs, and nonhuman primates, such as chimpanzees, may be used to practice the embodiments described herein. In a particular embodiment, the transgenic non-human animal is a mouse. The transgenic non-human animals described herein include individual animals in all stages of development, including embryonic and fetal stages.

A "transgenic animal" is an animal containing one or more cells bearing genetic information received, directly or indirectly, by deliberate genetic manipulation at a subcellular level, such as by microinjection or infection with a recombinant virus. The introduced nucleic acid molecule may be integrated within a chromosome, or it may be extra-chromosomally replicating DNA. Suitable transgenic animals described herein include, but are not limited to, those animals in which the genetic information was introduced into a germ line cell, thereby conferring the ability to transfer the information to offspring. If such offspring in fact possess some or all of that information, then they, too, are transgenic animals.

To produce transgenic animals, any method known in the art for introducing a recombinant construct or transgene into an embryo, such as, for example, microinjection, use of a cell gun, transfection, liposome fusion, electroporation, and the like, may be used. In a particular embodiment, the method for producing a transgenic animal is microinjection, which involves injecting a DNA molecule into the male pronucleus of a fertilized egg (see, e.g., U.S. Pat. Nos. 4,870,009; 5,550,316; 4,736,866; and 4,873,191). Methods for introducing a recombinant construct/transgene into mammals and their germ cells were originally developed in the mouse. Such methods were subsequently adopted for use with larger animals, including livestock species (see, e.g., PCT Publications Nos. WO 88/00239, WO 90/05188 and WO 92/11757). Microinjection of DNA into the cytoplasm of a zygote can also be used to produce transgenic animals.

The methods for evaluating the presence of the introduced transgene as well as its expression are readily available and well-known in the art. Such methods include, but are not limited to, DNA (Southern) hybridization to detect the exogenous DNA, polymerase chain reaction (PCR), polyacrylamide gel electrophoresis (PAGE) and blots to detect DNA, RNA or protein.

The present embodiments are not limited to any one species of animal, but provides for any appropriate non-human vertebrate species. For example, as described and exemplified herein, transgenic mice can be produced. Other non-limiting examples include, e.g., other non-human mammals described herein, such as guinea pigs, rabbits, pigs, sheep, etc. The success rate for producing transgenic animals by microinjection is highest in mice, where approximately 25% of fertilized mouse eggs into which the DNA has been injected, and which have been implanted in a female, will develop into transgenic mice. Lower success rates have been achieved with rabbits, pigs, sheep and cattle.

In a particular embodiment, the transgenic non-human animals described herein exhibit an expanded population of $B220^{low}/CD19^{low}/CD10^{low}/IgM^-/TCR^-/CD43^-$ lymphoid cells in the spleen, the bone marrow or both the spleen and bone marrow, relative to this population in a suitable control animal. As used herein, the term "expanded population of $B220^{low}/CD19^{low}/CD10^{low}/IgM^-/TCR^-/CD43^-$ cells" or "increase of $B220^{low}/CD19^{low}/CD10^{low}/IgM^-/TCR^-/CD43^-$ cells" refers to a population of lymphoid cells that represents an increase in the number of $B220^{low}/CD19^{low}/CD10^{low}/IgM^-/TCR^-/CD43^-$ cells and/or the proportion of $B220^{low}/CD19^{low}/CD10^{low}/IgM^-/TCR^-/CD43^-$ cells relative to other subtypes of lymphoid cells, as compared to that of a control animal.

In another embodiment, the transgenic non-human animals described herein exhibit a lymphoproliferative condition. "Lymphoproliferative" refers to that which pertains to, or is characterized by, proliferation of the cells of the lymphoreticular system; the term is generally used to refer to a group of malignant neoplasms. "Lymphoreticular" refers to the cells or tissues of both the lymphoid and reticuloendothelial systems. "Lymphoproliferative condition" (or "lymphoproliferative disease" or "lymphoproliferative disorder") refers to one of a group of malignant neoplasms arising from cells related to the common multipotential, primitive lymphoreticular cell that includes, among others, the lymphocytic, histiocytic, and monocytic leukemias, multiple myeloma, plasmacytoma, Hodgkin's disease, all lymphocytic lymphomas, and immunosecretory disorders associated with monoclonal gammopathy. As used herein, "lymphoproliferative disorder", "lymphoproliferative disease" or "lymphoproliferative condition" may also refer to a physiological state in which the proliferation, multiplication and/or accumulation of cells of the lymphoreticular system is altered relative to a normal or control animal, but the affected animal does not yet necessarily exhibit symptoms of one of the neoplasms described above. As used herein, a "preleukemic" state refers to such a lymphoproliferative condition that precedes the development of overt symptoms of leukemia.

In a certain embodiment, the lymphoproliferative condition is a B cell malignancy (e.g., a B cell leukemia (for example, acute lymphoblastic leukemia); a B cell lymphoma (e.g., high-grade lymphoma), a B cell neoplasm). In a further embodiment, the B cell malignancy exhibits characteristics of human acute lymphoblastic leukemia, human lymphoblastic lymphoma or a combination thereof. In yet another embodiment, the lymphoproliferative condition is a preleukemic state (e.g., pre-B cell proliferation). In additional embodiments, the transgenic non-human animal exhibits an enlarged abdomen, splenomegaly, bone marrow replacement, lymphopenia, or a combination thereof.

In another embodiment, there is described herein a method for the use of transgenic non-human animals as experimental models for the study of lymphoproliferative disorders (e.g., B cell malignancies (e.g., leukemias (e.g., acute lymphoblastic leukemia), lymphomas (e.g., high-grade lymphoma), and neoplasms)), and for testing potential carcinogenic and therapeutic agents.

In another aspect, there is described herein a method of testing the therapeutic efficacy of an agent in treating or preventing a lymphoproliferative condition in a subject. According to one embodiment, the method comprises administering the agent to a transgenic non-human animal (e.g., a mouse) described herein. In one embodiment, the transgenic non-human animal has a genome comprising a nucleic acid construct that comprises at least one transcriptional regulatory sequence capable of directing expression in B cells of the animal (e.g., a $V_H$ promoter, an Ig heavy chain-Eµ enhancer, a combination thereof), wherein the transcriptional regulatory sequence is operably linked to a nucleic acid encoding a miR155 gene product. In a particular embodiment, the transcriptional regulatory sequence is operably linked to a nucleotide sequence having at least 90% sequence identity to SEQ ID NO:1 and/or SEQ ID NO:2. In another embodiment, the miR155 gene product comprises the nucleotide sequence of SEQ ID NO:1. In yet another embodiment, the miR155 gene product comprises the nucleotide sequence of SEQ ID NO:2.

After the agent has been administered to the transgenic animal, one or more symptoms and/or indications of the lymphoproliferative condition in the transgenic animal are compared with those of a control animal of the same genotype, which has not been administered the agent. If the agent inhibits, prevents and/or reduces one or more symptoms and/or indications of the lymphoproliferative condition in the transgenic animal to which it has been administered, relative to the control animal, then the agent is considered to have therapeutic efficacy in treating or preventing a lymphoproliferative condition. In a certain embodiment, the one or more symptoms and/or indications of the lymphoproliferative condition are selected from the group consisting of: an expanded population of $B220^{low}/CD19^{low}/CD10^{low}/IgM^-/TCR^-/CD43^-$ lymphoid cells, enlarged abdomen, splenomegaly, bone marrow replacement, lymphopenia and a combination thereof.

Lymphoproliferative conditions that are suitable for testing the therapeutic efficacy of an agent include, for example, those described herein. In one embodiment, the lymphoproliferative condition is a B cell malignancy. In a particular embodiment, the B cell malignancy is selected from the group consisting of acute lymphoblastic leukemia, B cell lymphoma (e.g., high-grade lymphoma), B cell neoplasm and a combination thereof. The B cell malignancy may exhibit characteristics of human acute lymphoblastic leukemia, human lymphoblastic lymphoma or both. In another embodiment, the lymphoproliferative condition is a preleukemic state, such as a state characterized by pre-B cell proliferation.

As described herein, there is provided herein transgenic non-human animals that express miR155 in B cells. In one embodiment, a transgenic animal is provided whose genome comprises a nucleic acid construct or transgene comprising at least one transcriptional regulatory sequence capable of directing expression to B cells, wherein the transcriptional regulatory sequence is operably linked to a nucleic acid sequence encoding miR155. In a particular embodiment, the transgene comprises a DNA sequence encoding miR155 which has been placed under the transcriptional control of a $V_H$ promoter and/or an Ig heavy chain-Eµ enhancer. In such animals, mir155 expression is directed to immature and mature B cells. In one embodiment, the transgenic animals are mice which develop an expanded population of $B220^{low}/CD19^{low}/CD10^{low}/IgM^-/TCR^-/CD43^-$ lymphoid cells.

In another embodiment, white blood cells from a transgenic animal exhibiting lymphoproliferation may be transferred to a second animal (which may be a non-transgenic animal), thereby inducing a rapid onset of lymphoproliferative disease in the second "recipient" animal.

According to another embodiment, potential therapeutic modalities or agents for preventing and/or treating lymphoproliferative disorders may be tested by measuring the anti-lymphoproliferative activity of such modalities in animals produced according to one or more aspects as described herein. Such activity may be assessed by measuring the capacity of a potential therapeutic modality to inhibit, prevent, and/or destroy one or more of the symptoms or indications of lymphoproliferative disease exhibited by transgenic animals produced according to one embodiment and/or in "recipient" animals produced according to another embodiment.

A variety of therapeutic modalities or agents, such as proteins (e.g., antibodies), peptides, peptidomimetics, small organic molecules, nucleic acids and the like, can be tested for preventing and/or treating lymphoproliferative disorders. According to the methods described herein, agents can be individually screened or one or more agents can be tested simultaneously. Where a mixture of compounds is tested, the compounds selected by the processes described can be separated (as appropriate) and identified using suitable methods (e.g., sequencing, chromatography). The presence of one or more compounds in a test sample can also be determined according to these methods.

Agents that prevent and/or treat lymphoproliferative disorders can be identified, for example, by screening libraries or collections of molecules, such as, the Chemical Repository of the National Cancer Institute, in assays that measure inhibition and/or prevention of one or more of the symptoms or indications of lymphoproliferative disease exhibited by the transgenic animals described herein. Libraries, such as combinatorial libraries, of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678-2685 (1994) and references cited therein; see also, Ohlmeyer, M. H. J. et al., *Proc. Natl. Acad. Sci. USA*

90:10922-10926 (1993) and DeWitt, S. H. et al., *Proc. Natl. Acad. Sci. USA* 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a library carry unique tags, identification of individual compounds by chromatographic methods is possible.

Identified therapeutic modalities can further be formulated in accordance with known methods to produce pharmaceutically-acceptable compositions. Therapeutic modalities or compositions comprising such therapeutic modalities may be administered to subjects (e.g., transgenic animals) in a variety of standard ways. For example, the agent can be administered using a variety of routes, including, for example, oral, dietary, topical, transdermal, rectal, parenteral (e.g., intravenous, intraarterial, intramuscular, subcutaneous, intradermal injection), and inhalation (e.g., intrabronchial, intranasal, oral inhalation, intranasal drops). Administration can be local or systemic as indicated. The preferred mode of administration can vary depending upon the antibody or antigen-binding fragment to be administered and the particular condition (e.g., disease) being treated, however, oral or parenteral administration is generally preferred.

Agents can be administered parenterally such as, for example, by intravenous, intramuscular, intrathecal or subcutaneous injection. Parenteral administration can be accomplished by incorporating the agent(s) into a solution or suspension. Such solutions or suspensions may also include sterile diluents, such as water for injection, saline solution, bacteriostatic saline (saline containing about 0.9% mg/ml benzyl alcohol), phosphate-buffered saline (referred to herein as PBS), Hank's solution, Ringer's-lactate, fixed oils, polyethylene glycols, glycerine, propylene glycol, and other synthetic solvents. Parenteral formulations may also include antibacterial agents (e.g., benzyl alcohol, methyl parabens), antioxidants (e.g., ascorbic acid, sodium bisulfite), and chelating agents (e.g., EDTA). Buffers, such as acetates, citrates or phosphates and agents for the adjustment of tonicity such as sodium chloride and dextrose, may also be added. The parenteral preparation can be enclosed in ampules, disposable syringes, or multiple dose vials made of glass or plastic.

EXEMPLIFICATION

Example 1

Production of Eµ-mmu-miR155 Transgenic Mice

Figure 2A:
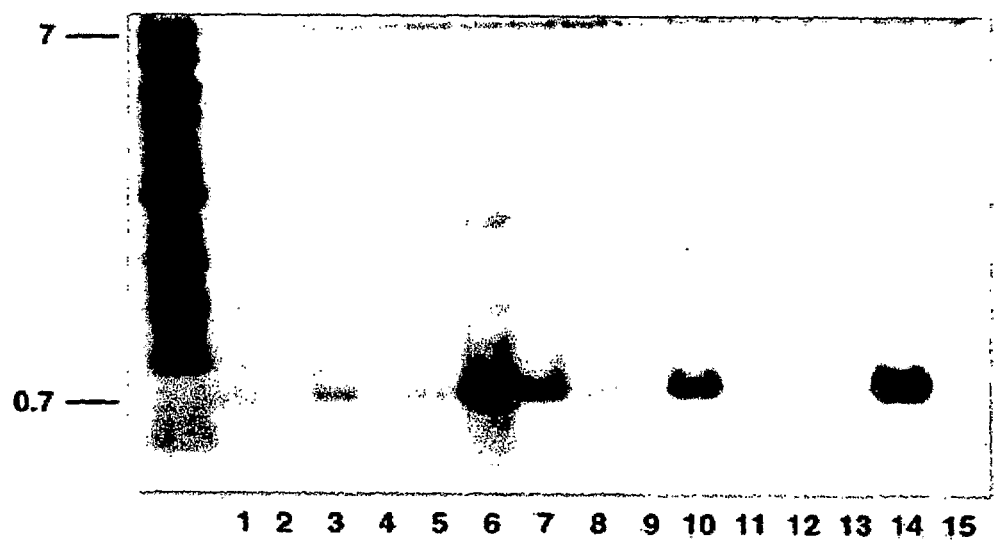
FIG. 2A is a Southern blot depicting the genotype of the seven miR155 transgenic founders (lanes 1, 3, 5, 6, 7, 10 and 14) and eight wild-type (lanes 2, 4, 8, 9, 11, 12, 13 and 15) mice with a C57BL/6 background.
Figure 2B:
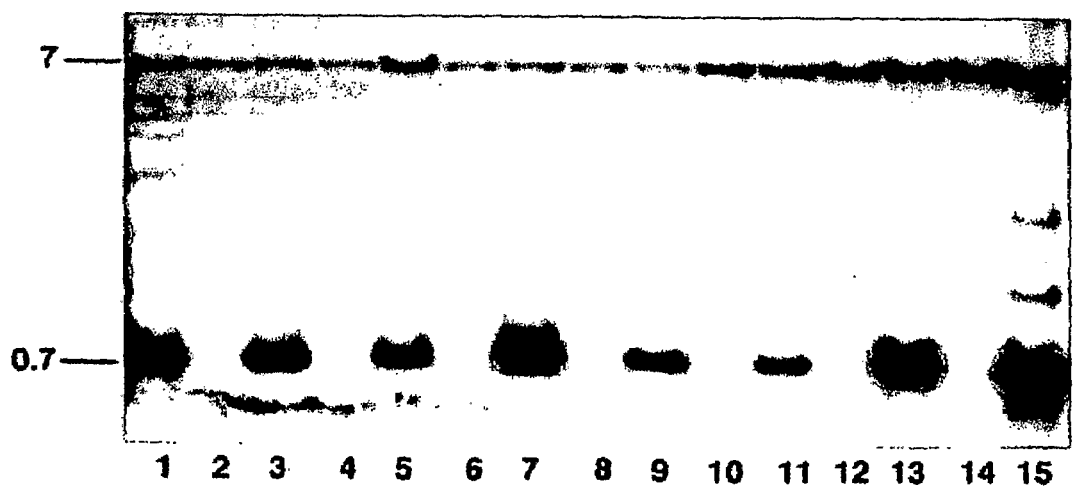
FIG. 2B is a Southern blot depicting the genotype of eight miR155 transgenic founders (lanes 1, 3, 5, 7, 9, 11, 13 and 15) and seven wild-type (lanes 2, 4, 6, 8, 10, 12 and 14) mice with an FVB/N background.

Materials and Methods
Transgenic Mice:
A 318-bp fragment containing the precursor sequence of miR155 was amplified by PCR from the genome of the 129SvJ mouse (The Jackson Laboratory) and cloned into the EcoRV and SalI sites of the pBSVE6BK (pEµ) plasmid, which contains the Eµ enhancer $V_H$ promoter for Ig heavy chains and the 3' UTR and the poly(A) of the human β-globin gene (FIG. 1), and had been used previously for the development of chronic lymphocytic leukemia in Eµ-TCL1 transgenic mice (Bichi, R., et al., *Proc. Natl. Acad. Sci. USA* 99:6955-6960 (2002)). The transgene, which was isolated by cutting the construct with BssHII and PvuI, was injected into the male pronucleus of fertilized oocytes of pregnant FVB/N and C57/B6 mice. Pups were screened for the presence of the transgene by Southern blot analysis, which was performed on tail-extracted DNA that was digested with BamHI, using a probe designed to target the Eµ enhancer sequence (FIGS. 2A, 2B). Transgenic founders were identified and bred to age-matched wild-type mice. Transgenic hemizygous mice were born, studied, and compared with their wild-type counterparts. Mice were genotyped by PCR performed on tail-extracted DNA (data not shown).

Figure 3:
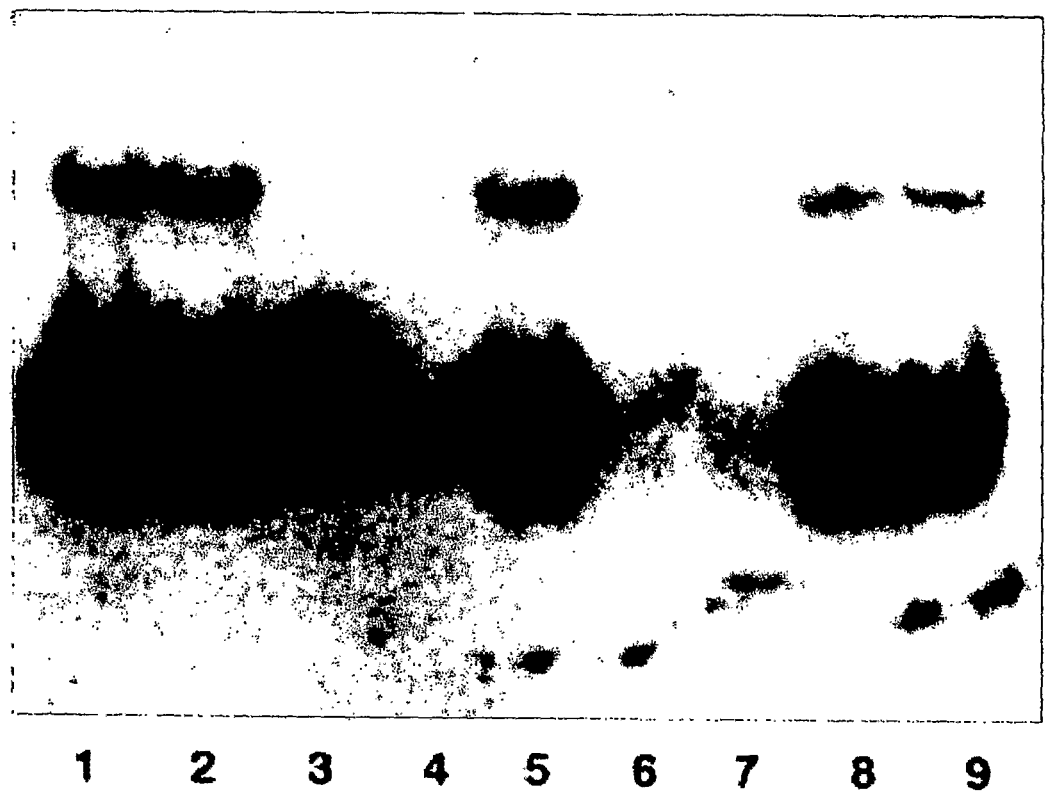
FIG. 3 is a Northern blot on total RNA depicting expression of mature miR155 in lymphocytes that were isolated from the spleens of 3-week-old mice from 6 of the 15 transgenic lines, using the antisense oligonucleotide of the mmu-miR155 mature sequence as a probe. The five transgenic lines with the highest level of expression of mature miR155 in the splenocytes (lanes 1, 2, 5, 8 and 9) were selected for further breeding and analysis. One transgenic line did not express the transgene (lane 3). Transgene expression was absent from the wild-type controls (lanes 4, 6 and 7).

Northern Blot Analysis:
Spleens were dissociated between two frosted slides, and the lysate was washed in phosphate buffered saline (PBS), depleted of red blood cells by hypotonic lysis with ammonium chloride ($NH_4Cl$), centrifuged, and resuspended in PBS. Total RNA was extracted with TRIzol Reagent (GIBCO, Invitrogen), loaded and denatured on SDS/PAGE, and blotted on a Hybond N+ membrane (Amersham Pharmacia). The membrane was hybridized with a $\gamma$-$^{32}$P radioactive probe containing the antisense of the mature mmu-miR155 sequence, incubated overnight, washed, and exposed to a PhosphorImager screen (Molecular Dynamics). The image was processed using a Typhoon image processing system (Amersham Biosciences) (FIG. 3).

Results
Transgenic mice were generated in which mmu-miR155 (mouse miR155) expression is under the control of a $V_H$ promoter-Ig heavy chain Eµ enhancer, which becomes active at the late pro-B cell stage of B cell development. Fifteen transgenic founders were identified by Southern blot hybridization (FIGS. 2A, 2B), seven on a C57BL/B6 background (designated F1-F7) and eight on an FVB/N background (designated F8-F15). These founders were bred to wild-type mice of the same strain to produce 15 independent transgenic lines.

Real-time PCR (data not shown) and Northern blot analysis (FIG. 3), performed on total RNA that was extracted from transgenic and wild-type spleens, showed high levels of miR155 expression for five founder lines of transgenic mice. One transgenic line lacked expression completely, while all other founder lines expressed the transgene. Wild-type mice did not express mature miR155 in the splenocytes, as previously reported (Monticelli, S., et al., *Genome Biol.* 6:R71 (2005)).

Example 2

Phenotypic Characterization of Eµ-mmu-miR155 Transgenic Mice Reveals a Pre-B Cell Proliferation in Spleens and Bone Marrow, Leading to B Cell Malignancies Materials and Methods
Somatic Measurements:
Mice were weighed after being killed, and their spleens were dissected, measured and weighed.

White Blood Cell (WBC) and Smear Preparation:
Blood was drawn from retroorbital blood vessels of mice and either smeared on frosted slides and stained with Giemsa or centrifuged, washed in PBS, and treated with ammonium chloride. Cells were counted with a cell-counter chamber.

Flow Cytometry Analysis:
Single-cell suspensions of splenocytes or bone marrow cells were depleted of mature red blood cells by hypotonic lysis (0.165 M $NH_4Cl$) and stained with the following conjugated antibodies: anti-B220-PE, anti-IgM-FITC, anti-TCR-PE cy5, anti-CD5-PE, and anti-CD-43-FITC. All antibodies were obtained from BD PharMingen. Flow cytometry was carried out on a Becton Dickinson FACSCalibur, and data were analyzed using the Becton Dickinson FACS CONVERT 1.0 for Mac software.

Histology and Immunohistochemistry:
Spleens, femurs, and sternums were isolated from necropsied mice and fixed in 10% buffered formalin, included in paraffin, and then cut into 4 micron sections. The sections were stained with hematoxylin/eosin according to standard protocols. For the dewaxing step, sections were heated for 1 hour at 55° C., rehydrated through a graded ethanol series and distilled water, immersed in PBS, and then treated with 0.1% trypsin solution in Tris buffer for 30 min at 37° C. Endogenous peroxidase was blocked with 10% normal serum. CD43, B220, and VpreB1 (CD179a) antibodies (BD PharMingen) were used as primary antibodies. Secondary antibodies and diaminobenzidine were added according to the manufacturer's instruction.

Results

Figure 4A:
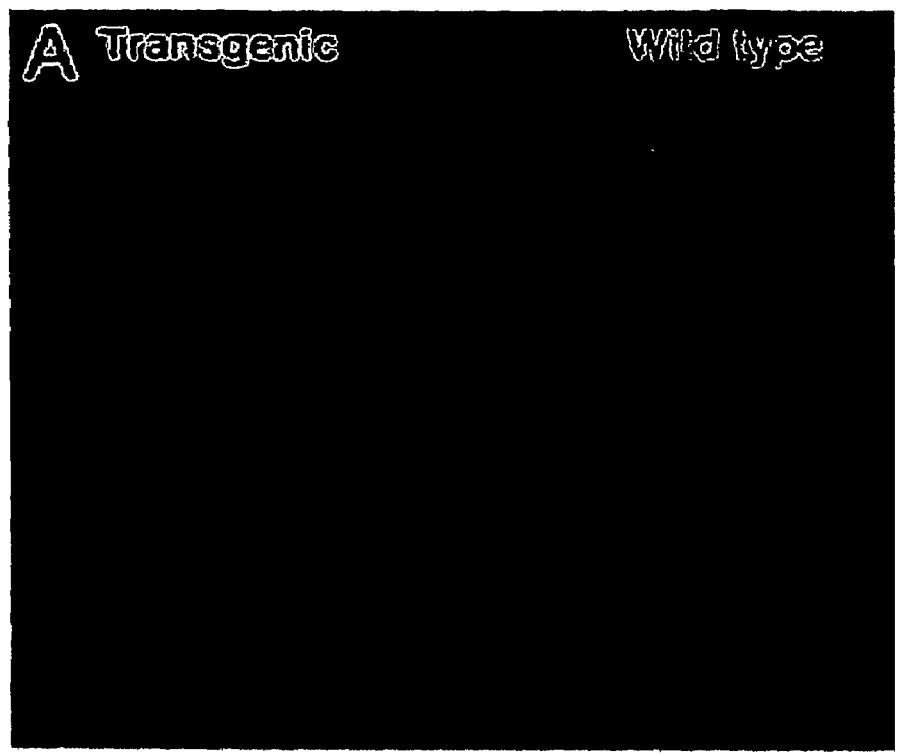
FIG. 4A is a photograph showing a transgenic mouse with a considerably enlarged abdomen (left), due to clinically-evident splenomegaly, relative to a wild-type mouse, at an age of 6 months.
Figure 4B:
FIG. 4B is a photograph depicting the spleens of the mice shown in FIG. 4A. The spleen of the transgenic mouse (left) is enlarged due to expansion of leukemic/lymphoma cells.

The bodies and spleens of transgenic mice were enlarged relative to the spleens of wild-type mice (FIGS. 4A, 4B), with a spleen weight/body weight ratio three to four times greater than the ratio of wild-type mice (Table 1). Interestingly, the ratio did not vary much with age.

TABLE 1

Spleen and body measurements for transgenic and wild-type mice.

| Mice | Line (founder) | Age, wks | BW, * gr | SW, ** mg | WI, *** mg/gr |
|---|---|---|---|---|---|
| 72tg | 8 | 3 | 22.68 | 210 | 9.25 |
| 69wt | 8 | 8 | 23.90 | 90 | 3.76 |
| 74tg | 8 | 3 | 23.98 | 270 | 11.25 |
| 68wt | 8 | 3 | 24.54 | 60 | 2.44 |
| 8gt | 8 | 24 | 38.3 | 380 | 9.92 |
| 24wt | N/A | 24 | 26.5 | 100 | 3.77 |
| 50tg | 10 | 3 | 21.7 | 200 | 9.21 |
| 49wt | 10 | 3 | 20.4 | 80 | 3.92 |
| 148wt | 8 | 6 | 26.97 | 240 | 8.89 |
| 149wt | 8 | 6 | 25.9 | 100 | 3.86 |
| 156tg | 10 | 6 | 23.44 | 280 | 11.94 |
| 157wt | 10 | 6 | 23.91 | 100 | 4.18 |
| 220wt | 8 | 7 | 23.13 | 120 | 5.2 |
| 221tg | 8 | 7 | 22.37 | 260 | 11.6 |
| 222tg | 8 | 7 | 21.67 | 250 | 11.5 |
| 223wt | 8 | 7 | 22.44 | 120 | 5.2 |

\* BW, body weight in grams (gr);
\*\* SW, spleen weight in milligrams (mg);
\*\*\* WI, weight index (ratio of weight trangenic to wild-type) in milligrams per gram (mg/g);
tg, transgenic mice;
wt, wild-type mice.

The white blood cell count (WBC) of 3-month-old transgenic mice was $10 \times 10^6 \pm 1 \times 10^6$ per ml of peripheral blood, compared with $40 \times 10^6 \pm 1.5 \times 10^6$ per ml of peripheral blood for normal, age-matched mice. The WBC for transgenic mice at 6 months of age was even lower, with a value of $6 \times 10^6 \pm 0.5 \times 10^6$ per ml of peripheral blood compared with an unchanged value of $40 \times 10^6 \pm 1.5 \times 10^6$ per ml of peripheral blood for wild-type, age-matched mice.

Histopathology of the spleens (hematoxylin/eosin stain) of 3-week-old transgenic mice featured a consistent atypical lymphoid population invading and expanding the red pulp. The germinal follicles were unaffected, and there were multiple foci of secondary hematopoiesis (FIG. 5A). Histologically, mice at 6 months of age presented a greatly increased malignant lymphoid population with marked atypia and blastic appearance, proliferating in the vascular channels of the red pulp and gradually replacing the white pulp. The number of germinal follicles was decreased, and the overall architecture of the spleen was distorted by lymphoid proliferation (FIG. 5B). A histologically-similar lymphoid population was present in the bone marrow of 6-month-old mice. Expression of the proliferation antigen, Ki67, showed a marked lymphoid proliferation in transgenic mice (FIG. 5D), which was not observed in wild-type mice.

Figure 6:
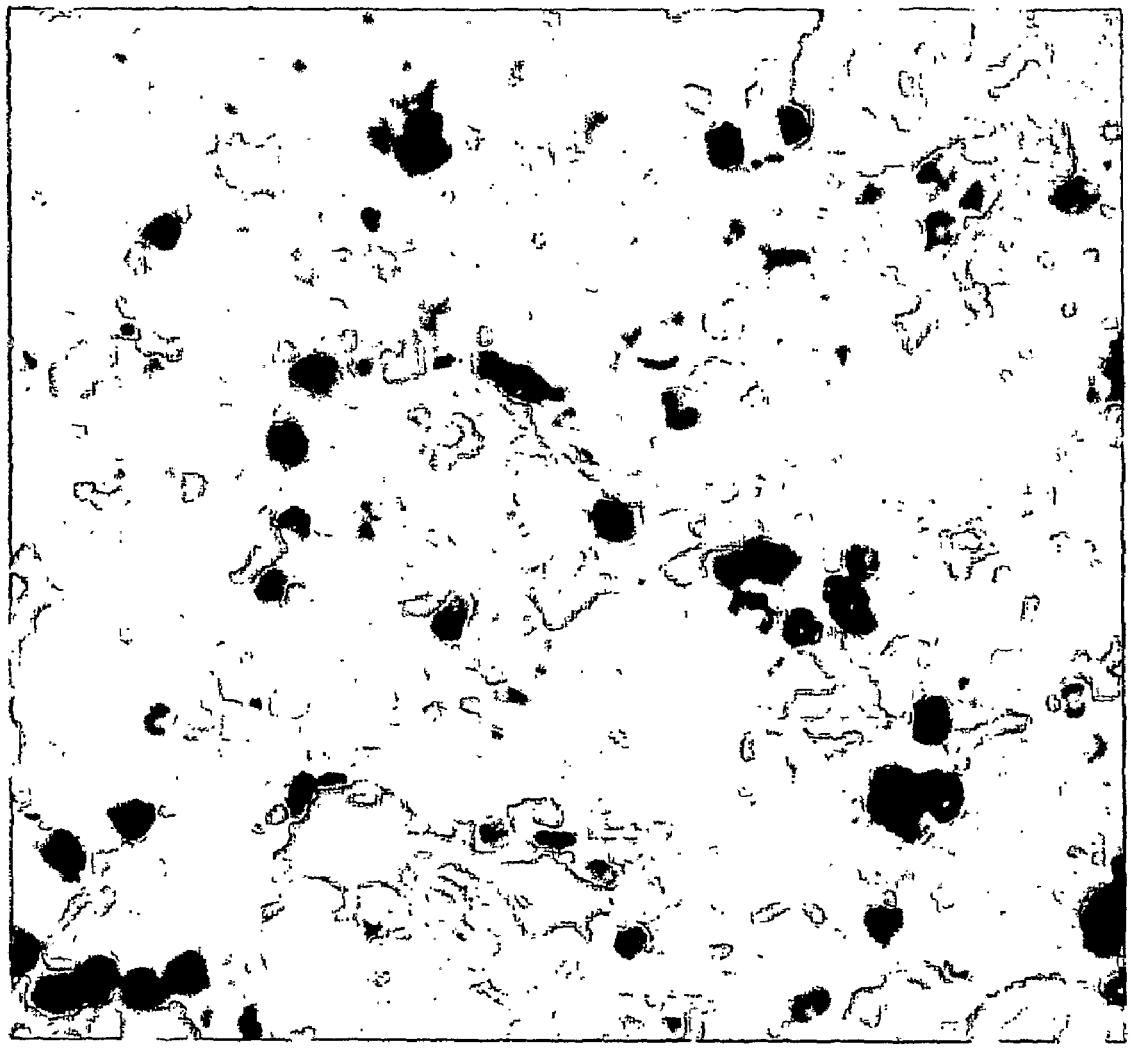
FIG. 6 is a micrograph at 400× magnification depicting atypical lymphoid proliferation in a section of spleen from a 3 week old transgenic mouse (mouse no. 50), which has been immunohistochemically-stained for IgM. IgM is present in the cytoplasm of the proliferating lymphocytes (cIgM) as a brown perinuclear halo in the transgenic mice, whereas the wild-type lymphocytes are intensely brown, with no distinct nuclei, due to the presence of both sIgM and cIgM.

Immunohistochemical analysis of lymphoid proliferation in the transgenic spleens showed low positivity of the atypical expanded lymphocytes for B220 and VpreB1 (CD179a), although CD43 was negative (data not shown). IgM staining of paraffin-embedded sections of the spleens of transgenic mice showed the presence of μ chains in the cytoplasm of the proliferating lymphocytes (FIG. 6). In contrast, flow cytometry analysis failed to identify the expression of IgM on the surface of these cells, indicating that the expanded lymphoid cells expressed cytoplasmic μ chain, but did not express surface IgM.

Flow cytometry analysis, performed on single-cell suspensions of WBC from the spleens and bone marrow of transgenic and wild-type mice at ages of 3, 6, or 7 weeks, or 6 months, showed an increase in the number of $B220^{low}/CD19^{low}/CD10^{low}/IgM^-/TCR^-/CD43^-$ lymphoid cells in both spleen and bone marrow in the transgenic mice, compared with their wild-type counterparts. This phenotype resembles the phenotype of proliferating lymphocytes observed in human acute lymphoblastic leukemia or lymphoblastic lymphoma. These findings indicate that the $B220^{low}/CD19^{low}/CD10^{low}/IgM^-/TCR^-/CD43^-$ lymphoid population in the spleens of transgenic mice at 3 weeks of age is 9% of the entire gated lymphoid population as compared to only 1.65% in the spleens of wild type mice (assessed on one transgenic and one wild-type mouse). At 6 weeks of age, these percentages become 6.6±1.4% in the spleen of transgenic mice and 4.7±0.3% for mice at 7 weeks of age, while remaining unchanged in wild-type spleens (two transgenic mice analyzed from two different founding lines and two wild-type mice).

Figure 7A:
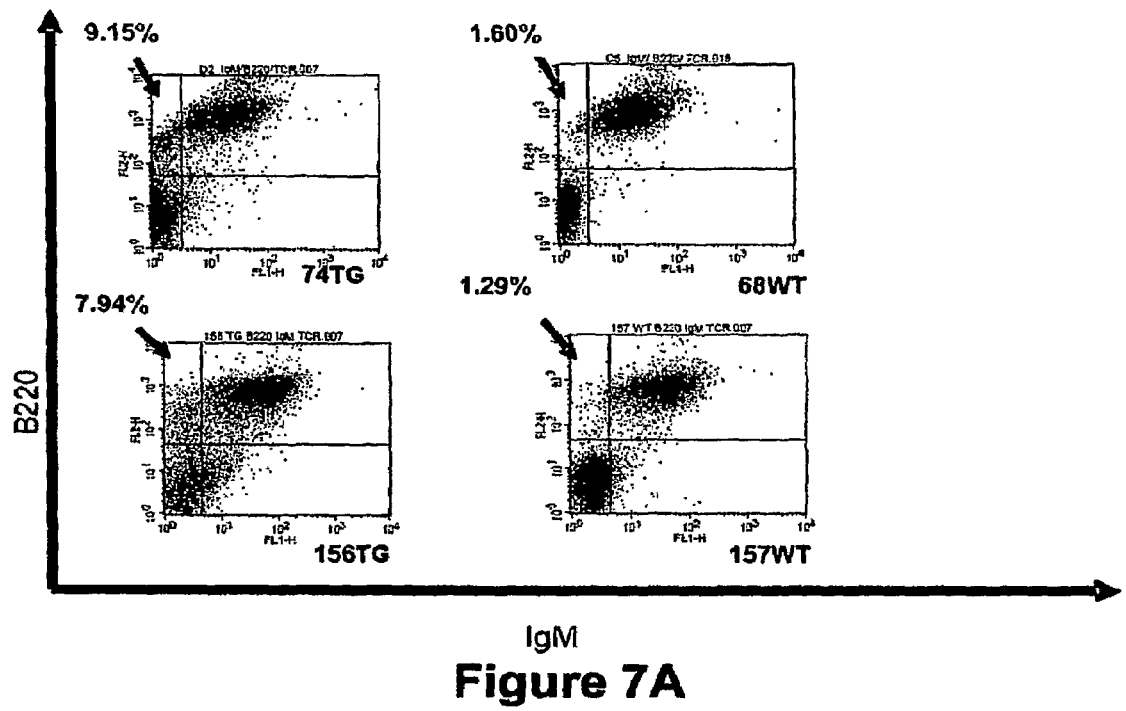
FIG. 7A is a flow cytometry analysis profile depicting an expansion of a $B220^{low}/CD19^{low}/CD10^{low}/IgM^-/TCR^-/CD43^-$ population of lymphocytes in the spleen of transgenic mice from two different lines of founders (founders 8 and 10). Gated splenocytes for two transgenic mice and two wild type mice at 3 weeks of age (transgenic mouse no. 74, founder 8 (74TG; upper left) and wild-type mouse no. 68 (68WT; upper right)) and 7 weeks of age (transgenic mouse no. 156, founder 10 (156TG; bottom left) and wild-type mouse no. 157 (157WT; bottom right)) are shown. Comparison of the upper left quadrants of the plots, gating the $B220^+$ IgM population, shows an increase in the number of precursor B cells in the transgenic spleen, relative to wild type.
Figure 7B:
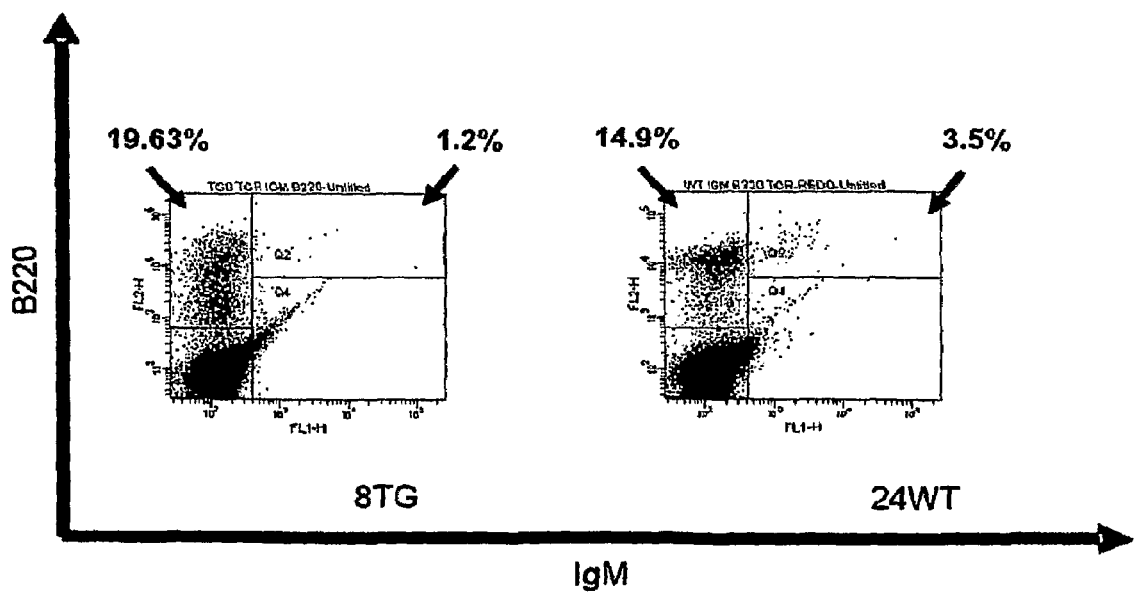
FIG. 7B is a flow cytometry analysis profile depicting an expansion of a $B220^{low}/CD19^{low}/CD10^{low}/IgM^-/TCR^-/CD43^-$ population of lymphocytes in the bone marrow of a transgenic mouse from founder 8. Gated bone marrow white blood cells for one transgenic and one wild-type mouse at 6 months of age (transgenic mouse no. 8, (8TG; left) and wild-type mouse no. 24 (24WT; right)) are shown. Comparison of the upper right quadrants of the two plots indicates a decrease in the $B200^+$ $IgM^+$ gated mature B cell population of the bone marrow of the transgenic mouse, relative to the wild-type mouse.
Figure 8A:
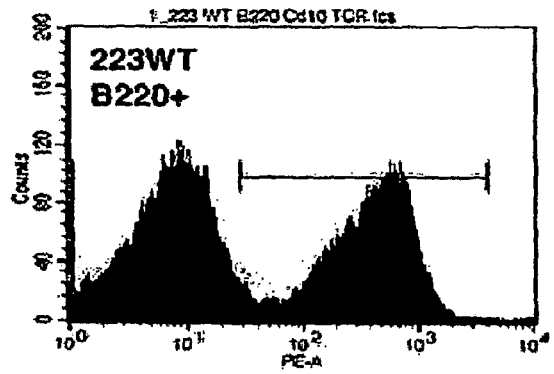
FIG. 8A is a graph depicting B220-PE expression as evaluated by flow cytometry analysis on $B220^+$-gated splenocytes of wild-type mouse no. 223 (223WT) at 7 weeks of age.
Figure 8B:
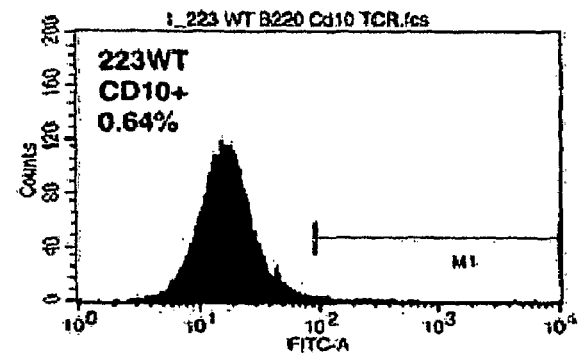
FIG. 8B is a graph depicting CD10-FITC expression as evaluated by flow cytometry analysis on $B220^+$-gated splenocytes of wild-type mouse no. 223 (223WT) at 7 weeks of age.
Figure 8C:
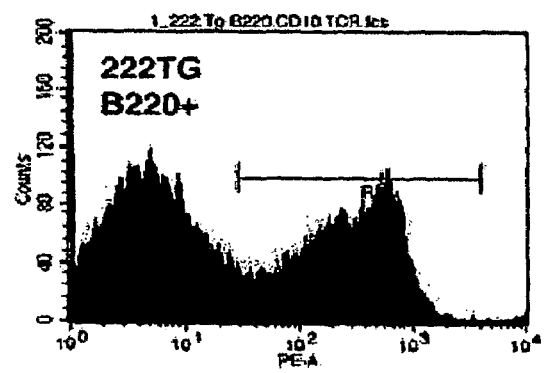
FIG. 8C is a graph depicting B220-PE expression as evaluated by flow cytometry analysis on $B220^+$-gated splenocytes of transgenic mouse no. 222 (222TG) at 7 weeks of age, showing a noticeable increase in the $B220^{low}$ population (intercalated between the two peaks of $B220^-$ and $B220^+$) in the transgenic mouse, relative to the wild-type mouse.
Figure 8D:
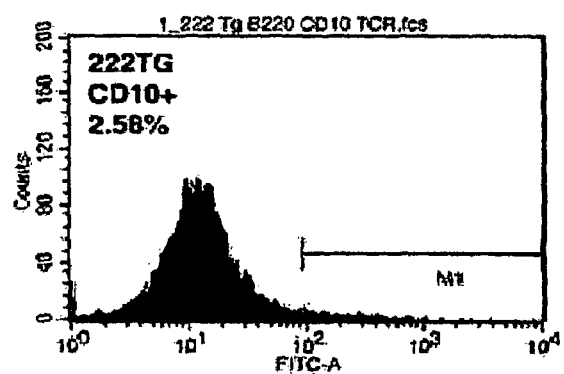
FIG. 8D is a graph depicting CD10-FITC expression as evaluated by flow cytometry analysis on $B220^+$-gated splenocytes of transgenic mouse no. 222 (222TG) at 7 weeks of age, showing an increase in the percentage of the $CD10^+$ population in the
$B220^+$-gated population only in the transgenic mouse relative to the wild-type mouse, demonstrating that the $B220^{low}$ proliferation is due, at least in part, to an increase of the $CD10^+$ population.
Figure 8E:
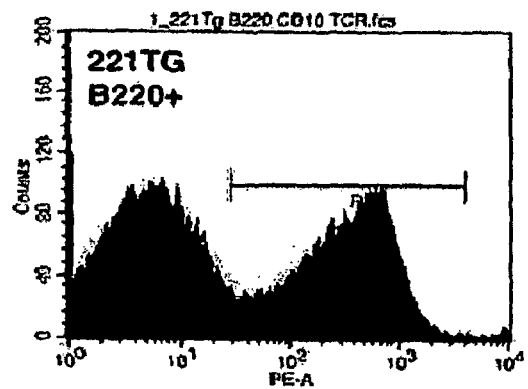
FIG. 8E is a graph depicting B220-PE expression as evaluated by flow cytometry analysis on $B220^+$-gated splenocytes of transgenic mouse no. 221 (221TG) at 7 weeks of age, showing a noticeable increase in the $B220^{low}$ population (intercalated between the two peaks of $B220^-$ and $B220^+$) in the transgenic mouse, relative to the wild-type mouse.
Figure 8F:
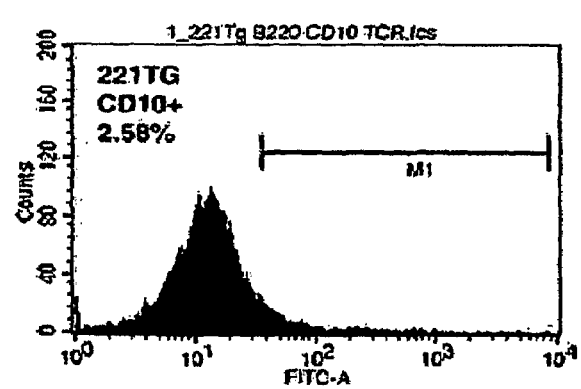
FIG. 8F is a graph depicting $CD10^+$ FITC expression as evaluated by flow cytometry analysis on $B220^+$-gated splenocytes of transgenic mouse no. 221 (221TG) at 7 weeks of age, showing an increase in the percentage of the $CD10^+$ population in the
$B220^+$-gated population only in the transgenic mouse relative to the wild-type mouse, demonstrating that the $B220^{low}$ proliferation is due, at least in part, to an increase of the $CD10^+$ population.

In the bone marrow of 6-month-old transgenic mice, we found an increase of the pre-B cell population as defined by $B220^{low}/IgM^-$ expression, compared with wild type (FIGS. 7 and 8). Forward-scatter analysis of the $B220^{low}/IgM^-$ cell population showed that these cells are large blastoid cells (data not shown).

Based on the flow cytometry, histological and immunohistochemical analyses, it was concluded that a pre-B cell proliferation, defined as $B220^{low}/CD19^{low}/CD10^{low}/IgM^-/TCR^-/CD43^-$, occurred in the spleens and bone marrows of transgenic mice and was already detectable at 3 weeks of age. This proliferation eventually resulted in splenomegaly, bone marrow replacement, and marked lymphopenia, features often associated with high-grade B cell malignancies. Consistent with this characterization, all of the transgenic mice developed high-grade B cell neoplasms by the age of 6 months (seven of seven transgenic mice) compared with the wild-type controls, which were all healthy (11 of 11 wild-type mice). Notably, the transgenic mouse line that did not overexpress miR155 was also normal.

Example 3

Cytogenetic Analysis of Eμ-mmu-miR155 Transgenic Mice

Materials and Methods

Cytogenetics:

Femur bone marrow was flushed with RPMI medium 1640/20% FBS and collected into 5 ml of RPMI medium 1640/20% FBS with 1% heparin. Cells were grown and assessed for chromosomal deletions, translocations, inversions, and number of metaphases using standard cytological techniques.

Ig Heavy Chain Rearrangements:

A probe was designed by amplifying a sequence in the JH4 fragment of the Ig heavy chain region of mouse genomic DNA using the following oligonucleotide primers:

```
forward,
                                    (SEQ ID NO:3)
5'-TGAAGGATCTGCCAGAACTGAA-3',
and reverse,
                                    (SEQ ID NO:4)
5'-TGCAATGCTCAGAAAACTCCAT-3'.
```

Spleens of the transgenic and wild-type mice were dissociated between frosted slides in PBS, treated with ammonium chloride to lyse erythrocytes, centrifuged, and resuspended in PBS. DNA was extracted from white blood cells of the spleens and digested with EcoRI, StuI, BglII, BamHI, and HindIII. Digested DNA was blotted on a Hybond N+ membrane, hybridized with the JH4 probe, which was radioactively labeled with $\gamma$-$^{32}$P, and then exposed to a PhosphorImager screen and processed using a Typhoon scanner.

Results

Figure 9:
FIG. 9 is a karyotype of lymphoid cells isolated from a transgenic spleen, analyzed for chromosomal deletions, translocations and inversions, as well as the number of metaphases. The arrow indicates an abnormality in Chromosome 9, which was identified by the presence of a thick extra band.

Cytogenetic studies of the karyotype of splenocytes failed to identify consistent chromosomal abnormalities in spleens from transgenic mice compared with the spleens from normal littermates. However, some genomic alterations were observed occasionally (FIG. 9; see arrow). These results indicate that the expanded population of pre-B cells is diploid and cytogenetically quasinormal.

Figure 10:
FIG. 10 is a Southern blot on DNA extracted from the splenocytes of 5 transgenic (TG) and 4 wild-type (WT) mice between 3 and 6 weeks of age. Southern blot hybridization was performed using the JH4 probe and different digesting enzymes, as indicated at the top of the lanes (StuI, BglII, BamHI, and HindIII). The thick bands of high molecular weight correspond to the germ line. There are no rearranged bands in the transgenic animals, relative to wild type.

To detect clonality, Southern blot analysis was performed on splenocyte DNA from mice between 3 and 6 weeks of age using multiple digestion enzymes to assess V(D)J rearrangements. The presence of rearranged bands in transgenic mice relative to wild-type mice were not detected (FIG. 10), with the exception of one transgenic mouse, which had a consistent rearranged band on Southern blots performed with each of the different restriction enzymes (data not shown). These data indicated that the B cell population in mice of this age was, for the most part, polyclonal, at least until 6 weeks of age. Because the majority of malignancies are monoclonal, this finding suggests that miR155 could be the downstream target of signal transduction pathways activated in cancer.

Interestingly, overexpression of miR155 has been observed in solid tumors, such as breast and colon cancer, as well as lung cancers, where overexpression of miR155 was an indicator of poor prognosis (Volinia, S., et al., *Proc. Natl. Acad. Sci. USA* 103:2257-2261 (2006)).

Example 4

Microarray Expression Profiling Reveals Up-Regulation of VpreB1 mRNA and Other Targets Materials and Methods RNA Isolation:

Total RNA isolation was performed with the TRIzol reagent (Invitrogen), according to the manufacturer's instructions.

miRNA Expression Profiling:

RNA labeling and hybridization on miRNA microarray chips were performed as described (Liu, C. G., et al., *Proc. Natl. Acad. Sci. USA* 101:9740-9744). Briefly, 5 µg of total RNA from each sample were labeled with biotin by reverse transcription using 5' biotin end-labeled random octamer oligonucleotide primers. Hybridization of biotin-labeled cDNA was carried out on a miRNA microarray chip (Ohio State University, Ver. 2.0), which contains 800 miRNA probes, including 245 human and 200 mouse miRNA genes, in quadruplicate. Hybridization signals were detected by binding of a Streptavidin-Alexa647 conjugate to biotin using Axon Scanner 4000B (Axon Instruments, Union City, Calif.). The images were quantified by GENEPIX 6.0 software (Axon Instruments).

mRNA Expression Profiling:

GeneChip Mouse genome 430 2.0 arrays (Affymetrix), containing probe sets for greater than 45,000 characterized genes and expressed sequence tags, were used. Sample labeling and processing, GeneChip hybridization, and scanning were performed according to Affymetrix protocols. Briefly, double-stranded cDNA was synthesized from total RNA using the SuperScript Choice System (Invitrogen), which adds a T7 RNA polymerase promoter site to the 3'-end (Genset, La Jolla, Calif.). Biotinylated cRNAs were generated from cDNAs in vitro and amplified using the BioArray T7 RNA polymerase labeling kit (Enzo Diagnostics). After purification of cRNAs using the RNeasy mini kit (Qiagen, Hilden, Germany), 20 µg of cRNA was fragmented at 94° C. for 35 min. Approximately 12.5 µg of fragmented cRNA was used in a 250-µl hybridization mixture containing herring-sperm DNA (0.1 mg/ml; Promega), plus bacterial and phage cRNA controls (1.5 pM BioB, 5 pM BioC, 25 pM BioD, and 100 µM Cre) to serve as internal controls for hybridization efficiency. Aliquots (200 µL) of the mixture were hybridized to arrays for 18 hours at 45° C. in a GeneChip Hybridization Oven 640 (Affymetrix). Each array was washed and stained with streptavidin-phycoerythrin (invitrogen) and amplified with biotinylated antistreptavidin antibody (Vector Laboratories) on the GeneChip Fluidics Station 450 (Affymetrix). Arrays were scanned with the GeneArray G7 scanner (Affymetrix) to obtain image and signal intensities.

Results

Microarray analysis was performed on total RNA extracted from the splenic white blood cells of five transgenic mice, including one mouse that did not express the miR155 transgene, and the white blood cells of six wild-type littermate counterparts. The analysis revealed a 10- to 20-fold increase in the expression of miR155, miR194, miR224, miR217, and miR151 (Table 3), and a 2- to 3-fold decrease in the expression of miR146 and miR138, in transgenic mice that overexpress miR155, relative to the wild-type littermate control mice (data not shown). Using an Affymetrix microarray chip, the differential expression of mRNAs in the same group of transgenic mice was studied and compared with mRNA expression in the littermate controls. The statistical analysis of the Affymetrix microarray data showed that 200 proliferation-associated genes were up-regulated, whereas 50 genes were down-regulated in the miR155-overexpressing mice (Table 3). Notably, VpreB1 mRNA was upregulated, which is expected to occur when the proliferation of pre-B cells takes place. These data complement the data from flow cytometry analysis and immunohistochemistry.

TABLE 2

Affymetrix microarray data for miR155 transgenic/wild-type mouse classification based on Prediction Analysis of Microarrays (PAM) (KDEL, DEAD and DEAH are disclosed as SEQ ID NOS 5-7, respectively).

| Name | Probe Set ID | Gene Title | mir155 score | wt score |
|---|---|---|---|---|
| 1456609_at | 1456609_at | RIKEN cDNA 1810006K23 gene | 0.8041* | −0.5744 |
| 1452324_at | 1452324_at | plasmacytoma variant translocation 1 | 0.4468* | −0.3192 |
| 1449452_a_at | 1449452_a_at | glycoprotein 2 (zymogen granule membrane) | 0.3377* | −0.2412 |
| 1459923_at | 1459923_at | brain expressed, X-linked 6 | 0.319* | −0.2279 |
| 1449222_at | 1449222_at | Epstein-Barr virus induced gene 3 | 0.31* | −0.2214 |
| 1424437_s_at | 1424437_s_at | ATP-binding cassette, sub-family G (WHITE), member 4 | 0.2723* | −0.1945 |
| 1425784_a_at | 1425784_a_at | olfactomedin 1 | 0.2717* | −0.1941 |
| 1436827_at | 1436827_at | gene model 944, (NCBI) | 0.2537* | −0.1812 |
| 1425677_a_at | 1425677_a_at | ankyrin 1, erythroid | 0.2513* | −0.1795 |
| 1417636_at | 1417636_at | solute carrier family 6 (neurotransmitter transporter, glycine), member 9 | 0.2476* | −0.1769 |
| 1441054_at | 1441054_at | apolipoprotein L, 2 | 0.233* | −0.1664 |
| 1458642_at | 1458642_at | killer cell lectin-like receptor family E member 1 | 0.2307* | −0.1648 |
| 1448558_a_at | 1448558_a_at | phospholipase A2, group IVA (cytosolic, calcium-dependent) | 0.2157* | −0.154 |
| 1418601_at | 1418601_at | aldehyde dehydrogenase family 1, subfamily A7 | 0.2136* | −0.1526 |
| 1458667_at | 1458667_at | RIKEN cDNA 4930519N13 gene | 0.2084* | −0.1488 |
| 1436443_a_at | 1436443_a_at | KDEL (Lys-Asp-Glu-Leu) containing 1 | 0.2073* | −0.1481 |
| 1416740_at | 1416740_at | procollagen, type V, alpha 1 | 0.2025* | −0.1447 |
| 1422663_at | 1422663_at | origin recognition complex, subunit 1-like (*S. cereviaiae*) | 0.2019* | −0.1442 |
| 1433892_at | 1433892_at | sperm associated antigen 5 | 0.1988* | −0.142 |
| 1435660_at | 1435660_at | similar to RIKEN cDNA 5830484A20 | 0.1979* | −0.1413 |
| 1454622_at | 1454622_at | solute carrier family 38, member 5 | 0.1847* | −0.132 |
| 1426802_at | 1426802_at | septin 8 | 0.1821* | −0.13 |
| 1449869_at | 1449869_at | pre-B lymphocyte gene 1 (VpreB1) | 0.1798* | −0.1284 |
| 1426015_s_at | 1426015_s_at | aspartate-beta-hydroxylase | 0.1768* | −0.1263 |
| 1418710_at | 1418710_at | CD59a antigen | 0.1697* | −0.1212 |
| 1437244_at | 1437244_at | Growth arrest-specific 2 like 3 | 0.1662* | −0.1187 |
| 1429830_a_at | 1429830_a_at | CD59a antigen | 0.1651* | −0.118 |
| 1422524_at | 1422524_at | ATP-binding cassette, sub-family B (MDR/TAP), member 6 | 0.1604* | −0.1145 |
| 1435287_at | 1435287_at | adducin 2 (beta) | 0.158* | −0.1129 |
| 1436984_at | 1436984_at | abl-interactor 2 | 0.1554* | −0.111 |
| 1453226_at | 1453226_at | RIKEN cDNA 3000004C01 gene | 0.1467* | −0.1048 |
| 1429146_at | 1429146_at | RIKEN cDNA 6620401M08 gene | 0.139* | −0.0993 |
| 1454630_at | 1454630_at | cDNA sequence BC034054 | 0.1385* | −0.099 |
| 1429089_s_at | 1429089_s_at | RIKEN cDNA 2900026A02 gene | 0.138* | −0.0986 |
| 1455980_a_at | 1455980_a_at | Growth arrest-specific 2 like 3 | 0.1375* | −0.0982 |
| 1427677_a_at | 1427677_a_at | SRY-box containing gene 6 | 0.1363* | −0.0974 |
| 1419031_at | 1419031_at | fatty acid desaturase 2 | 0.1338* | −0.0956 |
| 1422016_a_at | 1422016_a_at | centromere autoantigen H | 0.1309* | −0.0935 |
| 1420176_x_at | 1420176_x_at | immunoglobulin lambda-like polypeptide 1 | 0.1305* | −0.0932 |
| 1434501_at | 1434501_at | — | 0.1246* | −0.089 |
| 1419665_a_at | 1419665_a_at | nuclear protein 1 | 0.123* | −0.0878 |
| 1446391_at | 1446391_at | Synuclein, alpha | 0.1203* | −0.0859 |
| 1419421_at | 1419421_at | ankyrin 1, erythroid | 0.1181* | −0.0844 |
| 1452458_s_at | 1452458_s_at | peptidylprolyl isomerase (cyclophilin) like 5 | 0.1163* | −0.0831 |
| 1417939_at | 1417939_at | RAD51 associated protein 1 | 0.1149* | −0.0821 |
| 1436725_at | 1436725_at | RIKEN cDNA E130306D19 gene | 0.1104* | −0.0789 |
| 1437187_at | 1437187_at | E2F transcription factor 7 | 0.1103* | −0.0788 |
| 1453004_at | 1453004_at | RIKEN cDNA 3110004L20 gene | 0.1062* | −0.0758 |
| 1428105_at | 1428105_at | TPX2, microtubule-associated protein homolog (*Xenopus laevis*) | 0.1049* | −0.0749 |
| 1448926_at | 1448926_at | homeo box A5 | 0.1047* | −0.0748 |
| 1437370_at | 1437370_at | shugoshin-like 2 (*S. pombe*) | 0.1046* | −0.0747 |
| 1430999_a_at | 1430999_a_at | short coiled-coil protein | 0.1038* | −0.0742 |
| 1454757_s_at | 1454757_s_at | DNA segment, Chr 12, ERATO Doi 647, expressed | 0.1018* | −0.0727 |
| 1418026_at | 1418026_at | exonuclease 1 | 0.1016* | −0.0726 |
| 1435148_at | 1435148_at | ATPase, Na+/K+ transporting, beta 2 polypeptide | 0.1012* | −0.0723 |

TABLE 2-continued

Affymetrix microarray data for miR155 transgenic/wild-type mouse classification based on Prediction Analysis of Microarrays (PAM) (KDEL, DEAD and DEAH are disclosed as SEQ ID NOS 5-7, respectively).

| Name | Probe Set ID | Gene Title | mir155 score | wt score |
|---|---|---|---|---|
| 1434553_at | 1434553_at | RIKEN cDNA 4930577M16 gene | 0.1009* | −0.0721 |
| 1422967_a_at | 1422967_a_at | transferrin receptor | 0.1008* | −0.072 |
| 1434479_at | 1434479_at | expressed sequence AI413331 | 0.1001* | −0.0715 |
| 1431893_a_at | 1431893_a_at | trans-prenyltransferase | 0.0994* | −0.071 |
| 1447655_x_at | 1447655_x_at | SRY-box containing gene 6 | 0.0959* | −0.0685 |
| 1434789_at | 1434789_at | DEP domain containing 1B | 0.095* | −0.0678 |
| 1421957_a_at | 1421957_a_at | phosphate cytidylyltransferase 1, choline, alpha isoform | 0.0946* | −0.0676 |
| 1455228_at | 1455228_at | Wolf-Hirschhorn syndrome candidate 1 (human) | 0.0937* | −0.0669 |
| 1435663_at | 1435663_at | estrogen receptor 1 (alpha) | 0.093* | −0.0664 |
| 1429058_at | 1429058_at | RIKEN cDNA 1110004B13 gene | 0.0925* | −0.0661 |
| 1424229_at | 1424229_at | dual-specificity tyrosine-(Y)-phosphorylation regulated kinase 3 | 0.0919* | −0.0657 |
| 1422930_at | 1422930_at | intercellular adhesion molecule 4, Landsteiner-Wiener blood group | 0.0917* | −0.0655 |
| 1452591_a_at | 1452591_a_at | RIKEN cDNA 2410018G20 gene | 0.0905* | −0.0646 |
| 1453416_at | 1453416_at | growth arrest-specific 2 like 3 | 0.0886* | −0.0633 |
| 1433908_a_at | 1433908_a_at | cortactin | 0.0874* | −0.0624 |
| 1419595_a_at | 1419595_a_at | gamma-glutamyl hydrolase | 0.0872* | −0.0623 |
| 1421654_a_at | 1421654_a_at | lamin A | 0.0867* | −0.062 |
| 1417323_at | 1417323_at | RIKEN cDNA 5430413I02 gene | 0.085* | −0.0607 |
| 1450992_a_at | 1450992_a_at | myeloid ecotropic viral integration site 1 | 0.0832* | −0.0594 |
| 1435773_at | 1435773_at | RIKEN cDNA 4930547N16 gene | 0.0829* | −0.0592 |
| 1438711_at | 1438711_at | — | 0.0829* | −0.0592 |
| 1429701_at | 1429701_at | RIKEN cDNA 2410003J06 gene | 0.0827* | −0.0591 |
| 1433582_at | 1433582_at | RIKEN cDNA 1190002N15 gene | 0.0823* | −0.0588 |
| 1460192_at | 1460192_at | oxysterol binding protein-like 1A | 0.0817* | −0.0584 |
| 1443870_at | 1443870_at | ATP-binding cassette, sub-family C (CFTR/MRP), member 4 | 0.0814* | −0.0581 |
| 1456020_at | 1456020_at | SH3 domain and tetratricopeptide repeats 2 | 0.0813* | −0.0581 |
| 1451664_x_at | 1451664_x_at | killer cell lectin-like receptor subfamily A, member 12 //// killer cell lectin-like receptor, subfamily A, member 4 //// killer cell lectin-like receptor, subfamily A, member 7 //// killer cell lectin-like receptor subfamily A, member 20 //// killer cell lectin-like receptor, subfamily A, member 18 | 0.0812* | −0.058 |
| 1421975_a_at | 1421975_a_at | adducin 2 (beta) | 0.0805* | −0.0575 |
| 1423124_x_at | 1423124_x_at | RAD54 like (S. cerevisiae) | 0.0789* | −0.0563 |
| 1417749_a_at | 1417749_a_at | tight junction protein 1 | 0.0779* | −0.0557 |
| 1425145_at | 1425145_at | interleukin 1 receptor-like 1 | 0.0768* | −0.0549 |
| 1424722_at | 1424722_at | RIKEN cDNA 1300017J02 gene | 0.0762* | −0.0544 |
| 1455409_at | 1455409_at | spire homolog 1 (Drosophila) | 0.0739* | −0.0528 |
| 1453067_at | 1453067_at | RIKEN cDNA 2610040C18 gene | 0.0734* | −0.0524 |
| 1430839_at | 1430839_at | RIKEN cDNA 9430076G02 gene | 0.0713* | −0.0509 |
| 1434577_at | 1434577_at | cDNA sequence BC052040 | 0.0704* | −0.0503 |
| 1457306_at | 1457306_at | Polymerase (DNA directed), epsilon 3 (p17 subunit) | 0.0699* | −0.0499 |
| 1429734_at | 1429734_at | RIKEN cDNA 4632434I11 gene | 0.0695* | −0.0496 |
| 1449060_at | 1449060_at | kinesin family member 2C | 0.0684* | −0.0489 |
| 1424223_at | 1424223_at | RIKEN cDNA 1700020C11 gene | 0.0676* | −0.0483 |
| 1428372_at | 1428372_at | suppression of tumorigenicity 5 | 0.0667* | −0.0476 |
| 1436124_at | 1436124_at | phosphate cytidylyltransferase 1, choline, beta isoform | 0.0663* | −0.0474 |
| 1417656_at | 1417656_at | myeloblastosis oncogene-like 2 | 0.0661* | −0.0472 |
| 1436922_at | 1436922_at | — | 0.0657* | −0.047 |
| 1455009_at | 1455009_at | carboxypeptidase D | 0.065* | −0.0464 |
| 1434826_at | 1434826_at | expressed sequence AI256775 | 0.064* | −0.0457 |
| 1455746_at | 1455746_at | kinesin family member 13A | 0.0628* | −0.0449 |
| 1419087_s_at | 1419087_s_at | splicing factor 3a, subunit 1 | 0.0616* | −0.044 |
| 1418919_at | 1418919_at | shugoshin-like 1 (S. pombe) | 0.0611* | −0.0436 |
| 1433596_at | 1433596_at | DnaJ (Hsp40) homolog, subfamily C member 6 | 0.061* | −0.0436 |
| 1430538_at | 1430538_at | RIKEN cDNA 2210013O21 gene | 0.0605* | −0.0432 |
| 1454193_at | 1454193_at | RIKEN cDNA 5430401H09 gene | 0.0605* | −0.0432 |
| 1450380_at | 1450380_at | ependymin related protein 2 (zebrafish) | 0.06* | −0.0428 |

TABLE 2-continued

Affymetrix microarray data for miR155 transgenic/wild-type mouse
classification based on Prediction Analysis of Microarrays (PAM)
(KDEL, DEAD and DEAH are disclosed as SEQ ID NOS 5-7, respectively).

| Name | Probe Set ID | Gene Title | mir155 score | wt score |
|---|---|---|---|---|
| 1434322_at | 1434322_at | RIKEN cDNA A930021H16 gene | 0.0596* | −0.0426 |
| 1438650_x_at | 1438650_x_at | gap junction membrane channel protein alpha 1 | 0.0593* | −0.0424 |
| 1451914_a_at | 1451914_a_at | adducin 2 (beta) | 0.0574* | −0.041 |
| 1436584_at | 1436584_at | sprouty homolog 2 (*Drosophila*) | 0.0555* | −0.0396 |
| 1455012_s_at | 1455012_s_at | tripartite motif protein 37 | 0.0551* | −0.0394 |
| 1452026_a_at | 1452026_a_at | phospholipase A2, group XIIA | 0.0524* | −0.0374 |
| 1451257_at | 1451257_at | acyl-CoA synthetase long-chain family member 6 | 0.0521* | −0.0372 |
| 1435792_at | 1435792_at | component of Sp100-rs | 0.0513* | −0.0366 |
| 1435029_at | 1435029_at | RIKEN cDNA B230120H23 gene | 0.0492* | −0.0351 |
| 1434630_at | 1434630_at | ankyrin repeat domain 28 | 0.0491* | −0.0351 |
| 1426801_at | 1426801_at | septin 8 | 0.0483* | −0.0345 |
| 1436936_s_at | 1436936_s_at | inactive X specific transcripts | 0.0458* | −0.0327 |
| 1418069_at | 1418069_at | apolipoprotein C-II | 0.0456* | −0.0326 |
| 1425837_a_at | 1425837_a_at | CCR4 carbon catabolite repression 4 like (*S. cerevisiae*) | 0.0456* | −0.0326 |
| 1441757_at | 1441757_at | RIKEN cDNA 1190002F15 gene | 0.0454* | −0.0325 |
| 1422906_at | 1422906_at | ATP-binding cassette, sub-family G (WHITE), member 2 | 0.045* | −0.0322 |
| 1454858_x_at | 1454858_x_at | RIKEN cDNA 3300001H21 gene | 0.045* | −0.0321 |
| 1443673_x_at | 1443673_x_at | — | 0.0449* | −0.032 |
| 1417587_at | 1417587_at | timeless homolog (*Drosophila*) | 0.0447* | −0.0319 |
| 1456022_at | 1456022_at | homeodomain interacting protein kinase 2 | 0.0445* | −0.0318 |
| 1438202_at | 1438202_at | RIKEN cDNA C920005C14 gene | 0.0439* | −0.0314 |
| 1453836_a_at | 1453836_a_at | monoglyceride lipase | 0.0434* | −0.031 |
| 1422966_a_at | 1422966_a_at | transferrin receptor | 0.0431* | −0.0308 |
| 1439208_at | 1439208_at | checkpoint kinase 1 homolog (*S. pombe*) | 0.0423* | −0.0302 |
| 1422944_a_at | 1422944_a_at | diaphanous homolog 3 (*Drosophila*) | 0.0417* | −0.0298 |
| 1419412_at | 1419412_at | chemokine (C motif) ligand 1 | 0.0414* | −0.0296 |
| 1435378_at | 1435378_at | RIKEN cDNA 2210020M01 gene | 0.0414* | −0.0296 |
| 1422788_at | 1422788_at | solute carrier family 43, member 3 | 0.0413* | −0.0295 |
| 1452763_at | 1452763_at | non imprinted in Prader-Willi/Angelman syndrome 1 homolog (human) | 0.0413* | −0.0295 |
| 1428369_s_at | 1428369_s_at | Rho GTPase activating protein 21 | 0.0409* | −0.0292 |
| 1453107_s_at | 1453107_s_at | forkhead box M1 /// phosphatidylethanolamine binding protein /// RIKEN cDNA 4933413G19 gene | 0.0404* | −0.0288 |
| 1418219_at | 1418219_at | interleukin 15 | 0.0379* | −0.027 |
| 1448834_at | 1448834_at | forkhead box M1 | 0.0372* | −0.0266 |
| 1435054_at | 1435054_at | essential meiotic endonuclease 1 homolog 1 (*S. pombe*) | 0.0371* | −0.0265 |
| 1434586_a_at | 1434586_a_at | phosphatidylserine synthase 2 | 0.0367* | −0.0262 |
| 1418929_at | 1418929_at | estrogen-related receptor beta like 1 | 0.0366* | −0.0261 |
| 1451469_at | 1451469_at | RIKEN cDNA B430108F07 gene | 0.0363* | −0.0259 |
| 1428104_at | 1428104_at | TPX2, microtubule-associated protein homolog (*Xenopus laevis*) | 0.0339* | −0.0242 |
| 1427262_at | 1427262_at | inactive X specific transcripts | 0.0337* | −0.0241 |
| 1431012_a_at | 1431012_a_at | peroxisomal delta3, delta2-enoyl-Coenzyme A isomerase | 0.0336* | −0.024 |
| 1434850_at | 1434850_at | Hypothetical protein D030034H08 | 0.033* | −0.0236 |
| 1441520_at | 1441520_at | calmodulin binding protein 1 | 0.0329* | −0.0235 |
| 1423344_at | 1423344_at | erythropoietin receptor | 0.0328* | −0.0234 |
| 1434557_at | 1434557_at | huntingtin interacting protein 1 | 0.0325* | −0.0232 |
| 1424863_a_at | 1424863_a_at | homeodomain interacting protein kinase 2 | 0.0321* | −0.0229 |
| 1457670_s_at | 1457670_s_at | lamin A | 0.0316* | −0.0226 |
| 1451417_at | 1451417_at | breast cancer 1 | 0.0305* | −0.0218 |
| 1428952_at | 1428952_at | protein disulfide isomerase associated 2 | 0.0303* | −0.0217 |
| 1449514_at | 1449514_at | G protein-coupled receptor kinase 5 | 0.0296* | −0.0211 |
| 1416273_at | 1416273_at | tumor necrosis factor, alpha-induced protein 2 | 0.0292* | −0.0209 |
| 1460223_a_at | 1460223_a_at | erythrocyte protein band 4.9 | 0.0292* | −0.0208 |
| 1423902_s_at | 1423902_s_at | Rho guanine nucleotide exchange factor (GEF) 12 | 0.0291* | −0.0208 |
| 1417404_at | 1417404_at | ELOVL family member 6, elongation of long chain fatty acids (yeast) | 0.0289* | −0.0206 |

TABLE 2-continued

Affymetrix microarray data for miR155 transgenic/wild-type mouse
classification based on Prediction Analysis of Microarrays (PAM)
(KDEL, DEAD and DEAH are disclosed as SEQ ID NOS 5-7, respectively).

| Name | Probe Set ID | Gene Title | mir155 score | wt score |
|---|---|---|---|---|
| 1420712_a_at | 1420712_a_at | hepsin | 0.0273* | −0.0195 |
| 1452924_at | 1452924_at | RIKEN cDNA 2310007D09 gene | 0.0273* | −0.0195 |
| 1429059_s_at | 1429059_s_at | RIKEN cDNA 1110004B13 gene | 0.0272* | −0.0194 |
| 1435784_at | 1435784_at | autophagy-related 9-like 1 (yeast) | 0.0264* | −0.0189 |
| 1449648_s_at | 1449648_s_at | RNA polymerase 1-1 | 0.0264* | −0.0188 |
| 1460551_at | 1460551_at | RAN, member RAS oncogene family | 0.0259* | −0.0185 |
| 1439091_at | 1439091_at | Fanconi anemia, complementation group D2 | 0.0249* | −0.0178 |
| 1457851_at | 1457851_at | — | 0.0245* | −0.0175 |
| 1416575_at | 1416575_at | cell division cycle 45 homolog (*S. cerevisiae*)-like | 0.0234* | −0.0167 |
| 1422922_at | 1422922_at | RecQ protein-like 4 | 0.0234* | −0.0167 |
| 1456510_x_at | 1456510_x_at | UbiE-YGHL1 fusion protein | 0.0231* | −0.0165 |
| 1448871_at | 1448871_at | mitogen activated protein kinase 13 | 0.0226* | −0.0161 |
| 1450495_a_at | 1450495_a_at | killer cell lectin-like receptor subfamily K, member 1 | 0.0225* | −0.0161 |
| 1442000_at | 1442000_at | similar to novel protein | 0.0222* | −0.0158 |
| 1452098_at | 1452098_at | CTF18, chromosome transmission fidelity factor 18 homolog (*S. cerevisiae*) | 0.0219* | −0.0156 |
| 1453049_at | 1453049_at | RIKEN cDNA 6620401M08 gene | 0.0217* | −0.0155 |
| 1434864_at | 1434864_at | non imprinted in Prader-Willi/Angelman syndrome 1 homolog (human) | 0.0212* | −0.0152 |
| 1460495_s_at | 1460495_s_at | protease, serine, 25 | 0.021* | −0.015 |
| 1453181_x_at | 1453181_x_at | phospholipid scramblase 1 | 0.0209* | −0.0149 |
| 1420330_at | 1420330_at | C-type lectin domain family 4, member e | 0.0208* | −0.0149 |
| 1438011_at | 1438011_at | phosphate cytidylyltransferase 1, choline, alpha isoform | 0.0205* | −0.0146 |
| 1450344_a_at | 1450344_a_at | prostaglandin E receptor 3 (subtype EP3) | 0.0204* | −0.0146 |
| 1424895_at | 1424895_at | G-protein signalling modulator 2 (AGS3-like, *C. elegans*) | 0.0201* | −0.0144 |
| 1426543_x_at | 1426543_x_at | RIKEN cDNA 2310067E08 gene | 0.0193* | −0.0138 |
| 1423878_at | 1423878_at | glycophorin C | 0.0186* | −0.0133 |
| 1427263_at | 1427263_at | inactive X specific transcripts | 0.0186* | −0.0133 |
| 1434150_a_at | 1434150_a_at | RIKEN cDNA 3300001H21 gene /// UbiE-YGHL1 fusion protein | 0.0185* | −0.0132 |
| 1453681_at | 1453681_at | ATPase inhibitory factor 1 | 0.0181* | −0.013 |
| 1450556_at | 1450556_at | spectrin beta 1 | 0.0175* | −0.0125 |
| 1434554_at | 1434554_at | tripartite motif protein 37 | 0.0174* | −0.0124 |
| 1448529_at | 1448529_at | thrombomodulin | 0.0173* | −0.0123 |
| 1429404_at | 1429404_at | RIKEN cDNA 2010317E24 gene | 0.0168* | −0.012 |
| 1432886_at | 1432886_at | RIKEN cDNA 5730488B01 gene | 0.0162* | −0.0116 |
| 1435325_at | 1435325_at | ubiquitin specific protease 46 | 0.016* | −0.0114 |
| 1434587_x_at | 1434587_x_at | phosphatidylserine synthase 2 | 0.0157* | −0.0112 |
| 1418003_at | 1418003_at | RIKEN cDNA 1190002H23 gene | 0.0156* | −0.0111 |
| 1434310_at | 1434310_at | bone morphogenic protein receptor, type II (serine/threonine kinase) | 0.0147* | −0.0105 |
| 1435035_at | 1435035_at | RNA (guanine-9-) methyltransferase domain containing 2 | 0.0144* | −0.0103 |
| 1424413_at | 1424413_at | opioid growth factor receptor-like 1 | 0.014* | −0.01 |
| 1436872_at | 1436872_at | transforming, acidic coiled-coil containing protein 3 | 0.0133* | −0.0095 |
| 1417878_at | 1417878_at | E2F transcription factor 1 | 0.013* | −0.0093 |
| 1428433_at | 1428433_at | homeodomain interacting protein kinase 2 | 0.0125* | −0.0089 |
| 1429642_at | 1429642_at | AN1, ubiquitin-like, homolog (*Xenopus laevis*) | 0.0122* | −0.0087 |
| 1435786_at | 1435786_at | kelch-like 12 (*Drosophila*) | 0.0119* | −0.0085 |
| 1428391_at | 1428391_at | RAB3A interacting protein (rabin3)-like 1 | 0.0118* | −0.0085 |
| 1451596_a_at | 1451596_a_at | sphingosine kinase 1 | 0.0117* | −0.0084 |
| 1422619_at | 1422619_at | phosphatidic acid phosphatase 2a | 0.0111* | −0.0079 |
| 1449708_s_at | 1449708_s_at | checkpoint kinase 1 homolog (*S. pombe*) | 0.0106* | −0.0076 |
| 1429294_at | 1429294_at | thyroid hormone receptor interactor 13 | 0.0105* | −0.0075 |
| 1450862_at | 1450862_at | RAD54 like (*S. cerevisiae*) | 0.0103* | −0.0074 |
| 1433695_at | 1433695_at | RIKEN cDNA 1500041B16 gene | 0.0097* | −0.0069 |
| 1451083_s_at | 1451083_s_at | alanyl-tRNA synthetase | 0.0097* | −0.0069 |
| 1422620_s_at | 1422620_s_at | phosphatidic acid phosphatase 2a | 0.0094* | −0.0067 |
| 1457722_at | 1457722_at | RIKEN cDNA A630024B12 gene | 0.0091* | −0.0065 |

TABLE 2-continued

Affymetrix microarray data for miR155 transgenic/wild-type mouse
classification based on Prediction Analysis of Microarrays (PAM)
(KDEL, DEAD and DEAH are disclosed as SEQ ID NOS 5-7, respectively).

| Name | Probe Set ID | Gene Title | mir155 score | wt score |
| --- | --- | --- | --- | --- |
| 1455405_at | 1455405_at | proline-serine-threonine phosphatase-interacting protein 2 | 0.009* | −0.0064 |
| 1460010_a_at | 1460010_a_at | phosphatidylserine synthase 2 | 0.0089* | −0.0063 |
| 1424412_at | 1424412_at | opioid growth factor receptor-like 1 | 0.0083* | −0.0059 |
| 1456475_s_at | 1456475_s_at | protein kinase, cAMP dependent regulatory, type II beta | 0.0082* | −0.0058 |
| 1449714_at | 1449714_at | RIKEN cDNA 5730472N09 gene | 0.0077* | −0.0055 |
| 1434645_at | 1434645_at | RIKEN cDNA C530008M17 gene | 0.0069* | −0.005 |
| 1425157_x_at | 1425157_x_at | RIKEN cDNA 1300010A20 gene | 0.0067* | −0.0048 |
| 1432273_a_at | 1432273_a_at | Duffy blood group | 0.0063* | −0.0045 |
| 1417037_at | 1417037_at | origin recognition complex, subunit 6-like (S. cerevisiae) | 0.0062* | −0.0044 |
| 1428402_at | 1428402_at | zinc finger, CCHC domain containing 3 | 0.0062* | −0.0044 |
| 1416130_at | 1416130_at | prion protein | 0.0061* | −0.0043 |
| 1455218_at | 1455218_at | RIKEN cDNA 6330503K22 gene | 0.0056* | −0.004 |
| 1452166_a_at | 1452166_a_at | keratin complex 1, acidic, gene 10 | 0.0049* | −0.0035 |
| 1437992_x_at | 1437992_x_at | gap junction membrane channel protein alpha 1 | 0.0037* | −0.0026 |
| 1449015_at | 1449015_at | resistin like alpha | 0.0033* | −0.0023 |
| 1428713_s_at | 1428713_s_at | RIKEN cDNA 4833427B12 gene | 0.0032* | −0.0023 |
| 1427105_at | 1427105_at | RIKEN cDNA 2610510J17gene | 0.0031* | −0.0022 |
| 1426541_a_at | 1426541_a_at | RIKEN cDNA 2310067E08 gene | 0.0028* | −0.002 |
| 1424293_s_at | 1424293_s_at | RIKEN cDNA 2610319K07 gene | 0.0024* | −0.0017 |
| 1423724_at | 1423724_at | ZW10 interactor | 0.002* | −0.0014 |
| 1451609_at | 1451609_at | RIKEN cDNA 1300010A20 gene | 0.0018* | −0.0013 |
| 1417902_at | 1417902_at | solute carrier family 19 (thiamine transporter), member 2 | 0.0016* | −0.0012 |
| 1424292_at | 1424292_at | DEP domain containing 1a | 0.0015* | −0.0011 |
| 1455983_at | 1455983_at | cell division cycle associated 2 | 0.0015* | −0.0011 |
| 1448211_at | 1448211_at | ATPase, H+ transporting, lysosomal, V0 subunit E isoform 2 | 0.0013* | −9.00E−04 |
| 1453769_at | 1453769_at | RIKEN cDNA 2610318C08 gene | 0.0012* | −9.00E−04 |
| 1417892_a_at | 1417892_a_at | sirtuin 3 (silent mating type information regulation 2, homolog) 3 (S. cerevisiae) | 6.00E−04* | −4.00E−04 |
| 1428195_at | 1428195_at | RIKEN cDNA 4631427C17 gene | −1.00E−04# | 1.00E−04 |
| 1450932_s_at | 1450932_s_at | dedicator of cytokinesis 9 | −3.00E−04# | 2.00E−04 |
| 1417652_a_at | 1417652_a_at | tubulin cofactor a | −4.00E−04# | 3.00E−04 |
| 1455210_at | 1455210_at | zinc fingers and homeoboxes protein 2 | −0.0014# | 0.001 |
| 1419103_a_at | 1419103_a_at | abhydrolase domain containing 6 | −0.0015# | 0.001 |
| 1441975_at | 1441975_at | acid phosphatase, prostate | −0.0017# | 0.0012 |
| 1419119_at | 1419119_at | hematopoietic cell signal transducer | −0.0019# | 0.0013 |
| 1449508_at | 1449508_at | interleukin 27 receptor, alpha | −0.0025# | 0.0018 |
| 1445711_at | 1445711_at | expressed sequence BB163080 | −0.0029# | 0.002 |
| 1426044_a_at | 1426044_a_at | protein kinase C, theta | −0.0036# | 0.0026 |
| 1424903_at | 1424903_at | jumonji, AT rich interactive domain 1D (Rbp2 like) | −0.0037# | 0.0027 |
| 1416035_at | 1416035_at | — | −0.0045# | 0.0032 |
| 1460260_s_at | 1460260_s_at | karyopherin (importin) alpha 1 | −0.0046# | 0.0033 |
| 1439956_at | 1439956_at | Adult male aorta and vein cDNA, RIKEN full-length enriched library, clone: A530049N04 product: unknown EST, full insert sequence | −0.0048# | 0.0034 |
| 1416406_at | 1416406_at | phosphoprotein enriched in astrocytes 15 | −0.0051# | 0.0036 |
| 1419548_at | 1419548_at | karyopherin (importin) alpha 1 | −0.0054# | 0.0039 |
| 1437756_at | 1437756_at | GTPase, IMAP family member 9 | −0.0056# | 0.004 |
| 1436067_at | 1436067_at | zinc finger and BTB domain containing 10 | −0.0058# | 0.0042 |
| 1450710_at | 1450710_at | jumonji, AT rich interactive domain 2 | −0.0061# | 0.0044 |
| 1433955_at | 1433955_at | bromodomain and WD repeat domain containing 1 | −0.0067# | 0.0048 |
| 1439343_at | 1439343_at | 3 days neonate thymus cDNA, RIKEN full-length enriched library, clone: A630050A01 product: unclassifiable, full insert sequence | −0.0073# | 0.0052 |
| 1426771_at | 1426771_at | expressed sequence AI316828 | −0.0079# | 0.0057 |
| 1419722_at | 1419722_at | protease, serine, 19 (neuropsin) | −0.0085# | 0.0061 |
| 1419810_x_at | 1419810_x_at | Rho GTPase activating protein 9 | −0.0099# | 0.0071 |

TABLE 2-continued

Affymetrix microarray data for miR155 transgenic/wild-type mouse classification based on Prediction Analysis of Microarrays (PAM) (KDEL, DEAD and DEAH are disclosed as SEQ ID NOS 5-7, respectively).

| Name | Probe Set ID | Gene Title | mir155 score | wt score |
|---|---|---|---|---|
| 1452322_a_at | 1452322_a_at | bromodomain and WD repeat domain containing 1 | −0.0106# | 0.0076 |
| 1446835_at | 1446835_at | — | −0.011# | 0.0078 |
| 1417371_at | 1417371_at | pellino 1 | −0.0111# | 0.0079 |
| 1436353_at | 1436353_at | RIKEN cDNA A230046K03 gene | −0.0114# | 0.0082 |
| 1420685_at | 1420685_at | GRB2-related adaptor protein 2 | −0.0115# | 0.0082 |
| 1456440_s_at | 1456440_s_at | Transcribed locus | −0.0117# | 0.0084 |
| 1454742_at | 1454742_at | RasGEF domain family, member 1B | −0.0122# | 0.0087 |
| 1450024_at | 1450024_at | suppressor of fused homolog (*Drosophila*) | −0.0125# | 0.009 |
| 1433953_at | 1433953_at | zinc finger protein 277 | −0.0135# | 0.0096 |
| 1417210_at | 1417210_at | eukaryotic translation initiation factor 2, subunit 3, structural gene Y-linked | −0.0137# | 0.0098 |
| 1444828_at | 1444828_at | Protein phosphatase 2, regulatory subunit B (B56), gamma isoform | −0.0139# | 0.0099 |
| 1447502_at | 1447502_at | — | −0.014# | 0.01 |
| 1422445_at | 1422445_at | integrin alpha 6 | −0.0148# | 0.0106 |
| 1453244_at | 1453244_at | RIKEN cDNA 5830416P10 gene | −0.0157# | 0.0112 |
| 1426725_s_at | 1426725_s_at | E26 avian leukemia oncogene 1, 5' domain | −0.0175# | 0.0125 |
| 1438577_at | 1438577_at | Transcribed locus | −0.018# | 0.0129 |
| 1452077_at | 1452077_at | DEAD (Asp-Glu-Ala-Asp) box polypeptide 3, Y-linked | −0.02# | 0.0143 |
| 1416007_at | 1416007_at | special AT-rich sequence binding protein 1 | −0.0203# | 0.0145 |
| 1426438_at | 1426438_at | DEAD (Asp-Glu-Ala-Asp) box polypeptide 3, Y-linked | −0.021# | 0.015 |
| 1422122_at | 1422122_at | Fc receptor, IgE, low affinity II, alpha polypeptide | −0.0213# | 0.0152 |
| 1434260_at | 1434260_at | FCH and double SH3 domains 2 | −0.0215# | 0.0153 |
| 1417816_s_at | 1417816_s_at | tumor differentially expressed 1 | −0.0222# | 0.0158 |
| 1427532_at | 1427532_at | T cell receptor associated transmembrane adaptor 1 | −0.0222# | 0.0159 |
| 1454947_a_at | 1454947_a_at | cDNA sequence BC002236 | −0.0224# | 0.016 |
| 1418235_at | 1418235_at | autophagy-related 5-like (yeast) | −0.0243# | 0.0173 |
| 1418353_at | 1418353_at | CD5 antigen | −0.0258# | 0.0184 |
| 1450262_at | 1450262_at | cardiotrophin-like cytokine factor 1 | −0.026# | 0.0186 |
| 1455165_at | 1455165_at | Transcribed locus | −0.0268# | 0.0191 |
| 1439595_at | 1439595_at | T-cell receptor alpha chain | −0.0272# | 0.0194 |
| 1426620_at | 1426620_at | carbohydrate sulfotransferase 10 | −0.0278# | 0.0198 |
| 1454745_at | 1454745_at | Rho GTPase activating protein 29 | −0.029# | 0.0207 |
| 1439719_at | 1439719_at | RIKEN cDNA E430004N04 gene | −0.0292# | 0.0208 |
| 1435374_at | 1435374_at | Transcribed locus | −0.0302# | 0.0216 |
| 1456678_at | 1456678_at | RIKEN cDNA 1700091G21 gene | −0.0306# | 0.0218 |
| 1423176_at | 1423176_at | transducer of ErbB-2.1 | −0.0348# | 0.0249 |
| 1424374_at | 1424374_at | GTPase, IMAP family member 4 | −0.0355# | 0.0253 |
| 1446614_at | 1446614_at | Diacylglycerol kinase zeta | −0.0359# | 0.0257 |
| 1448862_at | 1448862_at | intercellular adhesion molecule 2 | −0.0365# | 0.0261 |
| 1439036_a_at | 1439036_a_at | ATPase, Na+/K+ transporting, beta 1 polypeptide | −0.0375# | 0.0268 |
| 1442023_at | 1442023_at | RIKEN cDNA A530030E21 gene | −0.0376# | 0.0269 |
| 1436182_at | 1436182_at | special AT-rich sequence binding protein 1 | −0.0385# | 0.0275 |
| 1443703_at | 1443703_at | Transcribed locus | −0.0385# | 0.0275 |
| 1422562_at | 1422562_at | Ras-related associated with diabetes | −0.0396# | 0.0283 |
| 1454893_at | 1454893_at | RIKEN cDNA 1110013L07 gene | −0.0402# | 0.0287 |
| 1427831_s_at | 1427831_s_at | zinc finger protein 260 | −0.0404# | 0.0289 |
| 1452163_at | 1452163_at | E26 avian leukemia oncogene 1, 5' domain | −0.0417# | 0.0298 |
| 1421570_at | 1421570_at | interleukin 9 receptor | −0.0431# | 0.0308 |
| 1442998_at | 1442998_at | Cytidine 5'-triphosphate synthase 2 | −0.0437# | 0.0312 |
| 1426452_a_at | 1426452_a_at | RAB30, member RAS oncogene family | −0.0473# | 0.0338 |
| 1431980_a_at | 1431980_a_at | arsenic (+3 oxidation state) methyltransferase | −0.0478# | 0.0341 |
| 1456205_x_at | 1456205_x_at | tubulin cofactor a | −0.048# | 0.0343 |
| 1441041_at | 1441041_at | RIKEN cDNA 2810407L07 gene | −0.0491# | 0.0351 |
| 1427418_a_at | 1427418_a_at | hypoxia inducible factor 1, alpha subunit | −0.0492# | 0.0351 |
| 1456502_at | 1456502_at | dual-specificity tyrosine-(Y)-phosphorylation regulated kinase 2 | −0.0502# | 0.0358 |

TABLE 2-continued

Affymetrix microarray data for miR155 transgenic/wild-type mouse
classification based on Prediction Analysis of Microarrays (PAM)
(KDEL, DEAD and DEAH are disclosed as SEQ ID NOS 5-7, respectively).

| Name | Probe Set ID | Gene Title | mir155 score | wt score |
|---|---|---|---|---|
| 1432229_a_at | 1432229_a_at | chromodomain protein, Y chromosome-like 2 | −0.0516# | 0.0368 |
| 1453726_s_at | 1453726_s_at | RIKEN cDNA 2810407C02 gene | −0.0517# | 0.0369 |
| 1440343_at | 1440343_at | ribosomal protein S6 kinase, polypeptide 5 | −0.0519# | 0.037 |
| 1435584_at | 1435584_at | expressed sequence AI662791 | −0.0522# | 0.0373 |
| 1419481_at | 1419481_at | selectin, lymphocyte | −0.0524# | 0.0374 |
| 1437907_a_at | 1437907_a_at | tubulin cofactor a | −0.0532# | 0.038 |
| 1419192_at | 1419192_at | interleukin 4 induced 1 | −0.0554# | 0.0395 |
| 1424936_a_at | 1424936_a_at | dynein, axonemal, heavy chain 8 | −0.0562# | 0.0402 |
| 1448931_at | 1448931_at | coagulation factor II (thrombin) receptor-like 1 | −0.0571# | 0.0408 |
| 1423890_x_at | 1423890_x_at | ATPase, Na+/K+ transporting, beta 1 polypeptide | −0.0582# | 0.0415 |
| 1458432_at | 1458432_at | Non-catalytic region of tyrosine kinase adaptor protein 2 | −0.0588# | 0.042 |
| 1440217_at | 1440217_at | similar to hypothetical protein FLJ39743 | −0.0593# | 0.0424 |
| 1440647_at | 1440647_at | signal-induced proliferation-associated 1 like 1 | −0.0596# | 0.0426 |
| 1440284_at | 1440284_at | Transcribed locus | −0.0598# | 0.0427 |
| 1457691_at | 1457691_at | Transcribed locus | −0.0614# | 0.0439 |
| 1455256_at | 1455256_at | TRAF2 and NCK interacting kinase | −0.0625# | 0.0447 |
| 1421628_at | 1421628_at | interleukin 18 receptor 1 | −0.0635# | 0.0454 |
| 1442045_at | 1442045_at | 16 days neonate thymus cDNA, RIKEN full-length enriched library, clone: A130046K23 product: unknown EST, full insert sequence | −0.0635# | 0.0453 |
| 1452737_at | 1452737_at | RIKEN cDNA 2810008M24 gene | −0.0673# | 0.0481 |
| 1419480_at | 1419480_at | selectin, lymphocyte | −0.0683# | 0.0488 |
| 1459632_at | 1459632_at | Cysteine-rich motor neuron 1 | −0.0722# | 0.0516 |
| 1427359_at | 1427359_at | RIKEN cDNA A630082K20 gene | −0.0757# | 0.0541 |
| 1426640_s_at | 1426640_s_at | tribbles homolog 2 (*Drosophila*) | −0.0783# | 0.0559 |
| 1435754_at | 1435754_at | DNA segment, Chr 6, Brigham & Women's Genetics 1452 expressed | −0.0791# | 0.0565 |
| 1460204_at | 1460204_at | cytoplasmic tyrosine kinase, Dscr28C related (*Drosophila*) | −0.0803# | 0.0574 |
| 1454897_at | 1454897_at | RIKEN cDNA 6330509M05 gene | −0.0804# | 0.0574 |
| 1449520_at | 1449520_at | expressed sequence AI428795 | −0.0813# | 0.058 |
| 1421622_a_at | 1421622_a_at | Rap guanine nucleotide exchange factor (GEF) 4 | −0.0841# | 0.0601 |
| 1425245_a_at | 1425245_a_at | regulator of G-protein signaling 11 | −0.0842# | 0.0602 |
| 1416008_at | 1416008_at | special AT-rich sequence binding protein 1 | −0.0847# | 0.0605 |
| 1452009_at | 1452009_at | RIKEN cDNA 9130422G05 gene | −0.0861# | 0.0615 |
| 1445141_at | 1445141_at | inhibitor of kappaB kinase beta | −0.0875# | 0.0625 |
| 1431169_at | 1431169_at | RIKEN cDNA D230012E17 gene | −0.0878# | 0.0627 |
| 1443192_at | 1443192_at | RIKEN cDNA E430004N04 gene | −0.0882# | 0.063 |
| 1428834_at | 1428834_at | dual specificity phosphatase 4 | −0.091# | 0.065 |
| 1423989_at | 1423989_at | RIKEN cDNA 2210010N04 gene | −0.0914# | 0.0653 |
| 1443573_at | 1443573_at | poly (ADP-ribose) polymerase family, member 1 | −0.0916# | 0.0654 |
| 1450061_at | 1450061_at | ectodermal-neural cortex 1 | −0.0959# | 0.0685 |
| 1452503_a_at | 1452503_a_at | bromodomain and WD repeat domain containing 1 | −0.0969# | 0.0692 |
| 1451313_a_at | 1451313_a_at | RIKEN cDNA 1110067D22 gene | −0.1008# | 0.072 |
| 1437253_at | 1437253_at | RIKEN cDNA A630054L15 gene | −0.1009# | 0.072 |
| 1428726_at | 1428726_at | THUMP domain containing 2 | −0.1017# | 0.0727 |
| 1451622_at | 1451622_at | LMBR1 domain containing 1 | −0.103# | 0.0736 |
| 1435456_at | 1435456_at | expressed sequence AI428795 | −0.1035# | 0.0739 |
| 1444181_at | 1444181_at | GTPase, IMAP family member 5 | −0.1036# | 0.074 |
| 1418762_at | 1418762_at | decay accelerating factor 1 | −0.1059# | 0.0757 |
| 1423297_at | 1423297_at | adducin 3 (gamma) | −0.1071# | 0.0765 |
| 1425518_at | 1425518_at | Rap guanine nucleotide exchange factor (GEF) 4 | −0.1071# | 0.0765 |
| 1427322_at | 1427322_at | bromodomain and WD repeat domain containing 1 | −0.1084# | 0.0775 |
| 1426158_at | 1426158_at | T-cell receptor beta, variable 13 | −0.1126# | 0.0804 |
| 1416129_at | 1416129_at | RIKEN cDNA 1300002F13 gene | −0.1139# | 0.0814 |
| 1426550_at | 1426550_at | SID1 transmembrane family, member 1 | −0.1143# | 0.0817 |

TABLE 2-continued

Affymetrix microarray data for miR155 transgenic/wild-type mouse
classification based on Prediction Analysis of Microarrays (PAM)
(KDEL, DEAD and DEAH are disclosed as SEQ ID NOS 5-7, respectively).

| Name | Probe Set ID | Gene Title | mir155 score | wt score |
|---|---|---|---|---|
| 1428510_at | 1428510_at | latrophilin 1 | −0.1187# | 0.0848 |
| 1456520_at | 1456520_at | RIKEN cDNA 9530033F24 gene | −0.1202# | 0.0859 |
| 1419212_at | 1419212_at | icos ligand | −0.126# | 0.09 |
| 1437540_at | 1437540_at | — | −0.1261# | 0.0901 |
| 1429969_at | 1429969_at | RIKEN cDNA 4833403J16 gene | −0.13# | 0.0929 |
| 1459722_at | 1459722_at | Zinc finger, SWIM domain containing 6 | −0.13# | 0.0928 |
| 1449642_at | 1449642_at | Epstein-Barr virus induced gene 2 | −0.1319# | 0.0942 |
| 1444283_at | 1444283_at | GTPase, IMAP family member 7 | −0.1324# | 0.0945 |
| 1434333_a_at | 1434333_a_at | protein kinase D2 | −0.1329# | 0.0949 |
| 1453119_at | 1453119_at | OTU domain containing 1 | −0.1339# | 0.0957 |
| 1421852_at | 1421852_at | potassium channel, subfamily K, member 5 | −0.1385# | 0.099 |
| 1425186_at | 1425186_at | LMBR1 domain containing 1 | −0.1443# | 0.103 |
| 1433977_at | 1433977_at | heparan sulfate (glucosamine) 3-O-sulfotransferase 3B1 | −0.1462# | 0.1044 |
| 1436491_at | 1436491_at | RIKEN cDNA 5830431A10 gene | −0.1518# | 0.1084 |
| 1460242_at | 1460242_at | decay accelerating factor 1 | −0.1524# | 0.1088 |
| 1445277_at | 1445277_at | 16 days neonate thymus cDNA, RIKEN full-length enriched library, clone: A130006J10 product: unknown EST, full insert sequence | −0.1527# | 0.1091 |
| 1418497_at | 1418497_at | fibroblast growth factor 13 | −0.1588# | 0.1134 |
| 1455425_at | 1455425_at | expressed sequence BB001228 | −0.1632# | 0.1166 |
| 1418998_at | 1418998_at | kynurenine 3-monooxygenase (kynurenine 3-hydroxylase) | −0.1673# | 0.1195 |
| 1452167_at | 1452167_at | RIKEN cDNA 2810407C02 gene | −0.1698# | 0.1213 |
| 1442266_at | 1442266_at | expressed sequence AI662175 | −0.1713# | 0.1223 |
| 1439843_at | 1439843_at | calcium/calmodulin-dependent protein kinase IV | −0.1732# | 0.1237 |
| 1427752_a_at | 1427752_a_at | T-cell receptor beta, variable 13 /// similar to TCRBV7S1 /// similar to TCRBV7S1 | −0.1805# | 0.1289 |
| 1451253_at | 1451253_at | PX domain containing serine/threonine kinase | −0.1819# | 0.1299 |
| 1428669_at | 1428669_at | brain expressed myelocytomatosis oncogene | −0.1862# | 0.133 |
| 1434967_at | 1434967_at | zinc finger, SWIM domain containing 6 | −0.1869# | 0.1335 |
| 1422231_a_at | 1422231_a_at | tumor necrosis factor receptor superfamily, member 25 | −0.1906# | 0.1361 |
| 1428914_at | 1428914_at | RIKEN cDNA 2310014D11 gene | −0.1917# | 0.1369 |
| 1434175_s_at | 1434175_s_at | RIKEN cDNA 2210010N04 gene | −0.2013# | 0.1438 |
| 1416268_at | 1416268_at | E26 avian leukemia oncogene 2,3' domain | −0.203# | 0.145 |
| 1436851_at | 1436851_at | protein kinase N1 | −0.2037# | 0.1455 |
| 1438862_at | 1438862_at | RIKEN cDNA A630005I04 gene | −0.2078# | 0.1484 |
| 1448107_x_at | 1448107_x_at | kallikrein 6 | −0.2085# | 0.149 |
| 1424062_at | 1424062_at | ubiquitin-conjugating enzyme E2D 1, UBC4/5 homolog (yeast) | −0.2114# | 0.151 |
| 1444003_at | 1444003_at | lung-inducible neuralized-related C3HC4 RING domain protein | −0.2133# | 0.1524 |
| 1428267_at | 1428267_at | DEAH (Asp-Glu-Ala-His) box polypeptide 40 | −0.2217# | 0.1584 |
| 1443906_at | 1443906_at | decay accelerating factor 1 | −0.2229# | 0.1592 |
| 1420583_a_at | 1420583_a_at | RAR-related orphan receptor alpha | −0.2261# | 0.1615 |
| 1420965_a_at | 1420965_a_at | ectodermal-neural cortex 1 | −0.2282# | 0.163 |
| 1446244_at | 1446244_at | DNA segment, Chr 6, Brigham & Women's Genetics 1452 expressed | −0.2305# | 0.1647 |
| 1440900_at | 1440900_at | Adult male thymus cDNA, RIKEN full-length enriched library, clone: 5830404C02 product: unknown EST, full insert sequence | −0.2324# | 0.166 |
| 1416958_at | 1416958_at | nuclear receptor subfamily 1, group D, member 2 | −0.2348# | 0.1677 |
| 1425832_a_at | 1425832_a_at | chemokine (C—X—C motif) receptor 6 | −0.2391# | 0.1708 |
| 1447792_x_at | 1447792_x_at | Adult male thymus cDNA, RIKEN full-length enriched library, clone: 5830404C02 product: unknown EST, full insert sequence | −0.2451# | 0.1751 |
| 1429443_at | 1429443_at | copine IV | −0.2472# | 0.1766 |
| 1455555_at | 1455555_at | expressed sequence AV071699 | −0.251# | 0.1793 |

TABLE 2-continued

Affymetrix microarray data for miR155 transgenic/wild-type mouse classification based on Prediction Analysis of Microarrays (PAM) (KDEL, DEAD and DEAH are disclosed as SEQ ID NOS 5-7, respectively).

| Name | Probe Set ID | Gene Title | mir155 score | wt score |
|---|---|---|---|---|
| 1415837_at | 1415837_at | kallikrein 6 | −0.2687# | 0.1919 |
| 1453568_at | 1453568_at | RIKEN cDNA 2310032F03 gene | −0.2765# | 0.1975 |
| 1452815_at | 1452815_at | purinergic receptor P2Y, G-protein coupled 10 | −0.2789# | 0.1992 |
| 1446412_at | 1446412_at | WW domain-containing oxidoreductase | −0.2819# | 0.2014 |
| 1448575_at | 1448575_at | interleukin 7 receptor | −0.2862# | 0.2044 |
| 1431050_at | 1431050_at | ribosomal protein S6 kinase, polypeptide 5 | −0.291# | 0.2078 |
| 1448576_at | 1448576_at | interleukin 7 receptor | −0.3125# | 0.2232 |
| 1422812_at | 1422812_at | chemokine (C—X—C motif) receptor 6 | −0.314# | 0.2243 |
| 1437356_at | 1437356_at | Epstein-Barr virus induced gene 2 | −0.322# | 0.23 |
| 1448613_at | 1448613_at | extracellular matrix protein 1 | −0.3377# | 0.2412 |
| 1433779_at | 1433779_at | cancer susceptibility candidate 4 | −0.4293# | 0.3066 |

The mir155 mRNA signature: * indicates the genes that are over-expressed in mouse mir155, # indicates the genes that are under-expressed. The score is the PAM score (Tibshirani, R. J., Hastie, T. J., Narasimhan, B., and Chu, G. (2002), "Diagnosis of multiple cancer types by shrunken centroids of gene expression," Proceedings of the National Academy of Sciences, 99, 6567-6572). PAM's method of "nearest shrunken centroids" identifies the subsets of genes that bestcharacterize the mir155 transgene. PAM's score is not a fold change.

TABLE 3

Affymetrix microarray data depicting signature of microRNAs that are significantly over-expressed in mir155 transgenic mice based on Prediction Analysis of Microarrays (PAM) classification (5 transgenic mice and 6 wild-type mice).

| Name | miR155 score | wt score |
|---|---|---|
| mmu-mir-151-prec | 3.9218* | −2.2411 |
| mmu-mir-217-precNo2 | 3.1565* | −1.8037 |
| mmu-mir-224-precformer175No1 | 1.9286* | −1.1021 |
| mmu-mir-194-prec | 1.6021* | −0.9155 |
| mmu-mir-201-prec | 1.5653* | −0.8945 |
| mmu-mir-155-prec | 1.4967* | −0.8553 |
| mmu-mir-218-2-precNo2 | 0.939* | −0.5365 |
| mmu-mir-182-prec | 0.4886* | −0.2792 |

The mir155 microRNA signature:
*indicates the microRNAs that are significantly over-expressed in Eμ-mmu-miR155 transgenic mice.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A transgenic mouse whose genome comprises a nucleic acid construct comprising at least one transcriptional regulatory sequence capable of directing expression in B cells of the mouse, wherein said transcriptional regulatory sequence is operably linked to a nucleic acid encoding a miR155 gene product comprising a nucleotide sequence having at least 90% sequence identity to SEQ ID NO: 1 and/or SEQ ID NO: 2, wherein said mouse exhibits a B cell malignancy.

2. The transgenic mouse of claim 1, wherein the at least one transcriptional regulatory sequence comprises a VH promoter.

3. The transgenic mouse of claim 1, wherein the at least one transcriptional regulatory sequence comprises an Ig heavy chain-Eµ enhancer.

4. The transgenic mouse of claim 1, wherein the nucleic acid encodes a miR155 gene product comprising SEQ ID NO: 1 and/or SEQ ID NO:2.

5. The transgenic mouse of claim 2 wherein the VH promoter is derived from mouse.

6. The transgenic mouse of claim 3, wherein the Ig heavy chain-Eµ enhancer is derived from mouse.

7. The transgenic mouse of claim 1, wherein the B cell malignancy is a leukemia, lymphoma or neoplasm.

8. The transgenic mouse of claim 1, wherein the nucleic acid construct comprises the 3' UTR and poly(A) sequence of the β-globin gene.

9. The transgenic mouse of claim 1, wherein the B cell malignancy exhibits characteristics of human acute lymphoblastic leukemia, human lymphoblastic lymphoma or a combination thereof.

10. A transgenic mouse whose genome comprises a nucleic acid construct comprising a VH promoter and an Ig heavy chain-Eµ enhancer, operably linked to a nucleic acid encoding a miR155 gene product comprising SEQ ID NO: 1 and/or SEQ ID NO:2.

11. A method of determining whether an agent affects a B cell malignancy, comprising:
  a) administering said agent to a transgenic mouse whose genome comprises a nucleic acid construct comprising at least one transcriptional regulatory sequence capable of directing expression in B cells of the mouse, operably linked to a nucleic acid encoding a miR155 gene product comprising a nucleotide sequence having at least 90% sequence identity to SEQ ID NO: 1 and/or SEQ ID NO: 2, wherein said mouse exhibits a B cell malignancy; and
  b) after said agent has been administered to said transgenic mouse, comparing one or more symptoms and/or indications of said B cell malignancy in said mouse to those of a control mouse of the same genotype, wherein the control mouse has not been administered said agent, wherein a difference in the detectability and/or rate of appearance of said one or more symptoms and/or indications of said B cell malignancy in said transgenic mouse, relative to said control mouse, is indicative of the agent affecting the B cell malignancy.

12. A method of testing the therapeutic efficacy of an agent in treating a B cell malignancy, comprising:
  a) administering said agent to a transgenic mouse whose genome comprises a nucleic acid construct comprising at least one transcriptional regulatory sequence capable of directing expression in B cells of the mouse, operably linked to a nucleic acid encoding a miR155 gene product comprising a nucleotide sequence having at least 90% sequence identity to SEQ ID NO: 1 and/or SEQ ID NO: 2, wherein said mouse exhibits a B cell malignancy; and
  b) after said agent has been administered to said transgenic mouse, comparing one or more symptoms and/or indications of said B cell malignancy in said mouse to those of a control mouse of the same genotype, wherein the control mouse has not been administered said agent, wherein if said agent inhibits, prevents and/or reduces said one or more symptoms and/or indications of said B cell malignancy in said mouse, relative to said control mouse, then said agent is considered to have therapeutic efficacy in treating or preventing a B cell malignancy.

13. The method of claim 12, wherein the at least one transcriptional regulatory sequence comprises a VH promoter, an Ig heavy chain-Eµ enhancer or a combination thereof.

14. The method of claim 12, wherein the transcriptional regulatory sequence is derived from mouse.

15. The method of claim 12, wherein the nucleic acid comprises the nucleotide sequence of SEQ ID NO:1 and/or SEQ ID NO:2.

16. The method of claim 12, wherein the B cell malignancy is selected from the group consisting of acute lymphoblastic leukemia, B cell lymphoma, B cell neoplasm and a combination thereof.

17. The method of claim 12, wherein the B cell malignancy exhibits characteristics of human acute lymphoblastic leukemia, human lymphoblastic lymphoma or a combination thereof.

18. The method of claim 13, wherein the at least one transcriptional regulatory sequence comprises a VH promoter, an Ig heavy chain-Eµ enhancer or a combination thereof.

19. The method of claim 13, wherein the transcriptional regulatory sequence is derived from mouse.

20. The method of claim 13, wherein the nucleic acid comprises the nucleotide sequence of SEQ ID NO: 1 and/or SEQ ID NO:2.

21. The method of claim 13, wherein the B cell malignancy is selected from the group consisting of acute lymphoblastic leukemia, B cell lymphoma, B cell neoplasm and a combination thereof.

22. The method of claim 13, wherein the B cell malignancy exhibits characteristics of human acute lymphoblastic leukemia, human lymphoblastic lymphoma or a combination thereof.

* * * * *